(12) United States Patent
Polonskiy et al.

(10) Patent No.: US 7,796,833 B2
(45) Date of Patent: Sep. 14, 2010

(54) METHOD FOR SPECTRAL DATA CLASSIFICATION AND DETECTION IN DIVERSE LIGHTING CONDITIONS

(75) Inventors: Leonid Polonskiy, Oakmont, PA (US); Zhu Joe Wang, Ballwin, MO (US); Jasenka Benac, St. Louis, MO (US); Jeffry Golden, Creve Coeur, MO (US)

(73) Assignee: CET, LLC, Earth City, MO (US)

( * ) Notice: Subject to any disclaimer, the term of this patent is extended or adjusted under 35 U.S.C. 154(b) by 881 days.

(21) Appl. No.: 11/676,225

(22) Filed: Feb. 16, 2007

(65) Prior Publication Data

US 2008/0046217 A1 Feb. 21, 2008

Related U.S. Application Data

(60) Provisional application No. 60/774,057, filed on Feb. 16, 2006.

(51) Int. Cl.
*G06K 9/40* (2006.01)
*G06K 9/46* (2006.01)
*G06K 9/62* (2006.01)
*G06K 9/00* (2006.01)

(52) U.S. Cl. .................. 382/274; 382/103; 382/207; 382/224

(58) Field of Classification Search .................. 382/103, 382/207, 224, 274; 702/2, 4
See application file for complete search history.

(56) References Cited

U.S. PATENT DOCUMENTS 2,540,797 A 2/1951 Stearns, Jr.
2,542,564 A 2/1951 Park
4,411,519 A 10/1983 Tagami (Continued)

FOREIGN PATENT DOCUMENTS

GB 2360660 B 12/2002

OTHER PUBLICATIONS

Lillesand, T. H. et al, "Remote Sensing and Image Interpretation", Fifth Edition, Chapter 7, John Wiley & Sons, New York, 2004, pp. 491-637.

(Continued)

*Primary Examiner*—John B Strege
(74) *Attorney, Agent, or Firm*—Grant D. Kang; Kang Intellectual Property Law, LLC

(57) ABSTRACT

The invention is a method of spectral data classification that uses the decoupling of target chromaticity and lighting or illumination chromaticity in spectral data and the sorting and selection of spectral bands by values of a merit function to obtain an optimized set of combinations of spectral bands for classification of the data. The decoupling is performed in "delta-log" space. A rotation transform may be applied. For a broad range of parameters, correction of lighting chromaticity may be obtained by use of an equivalent "Planck distribution" temperature. Merit function sorting and band combination selection is performed by multiple selection criteria. The method achieves reliable pixel classification and target detection in diverse lighting or illumination, especially in circumstances where lighting is non-uniform across a scene, such as with sunlight and shadows on a partly cloudy day or in "artificial" lighting. Applications are found in homeland security, defense, environmental protection, biomedical diagnostics, industrial process and product monitoring, and other remote or standoff sensing by spectral characteristics.

16 Claims, 13 Drawing Sheets

U.S. PATENT DOCUMENTS

| | | | |
|---|---|---|---|
| 4,488,245 | A | 12/1984 | Dalke et al. |
| 4,623,973 | A | 11/1986 | Hoffrichter et al. |
| 4,648,051 | A | 3/1987 | Wandell et al. |
| 4,653,925 | A | 3/1987 | Thornton, Jr. |
| 4,750,140 | A | 6/1988 | Asano et al. |
| 4,797,738 | A | 1/1989 | Kashi et al. |
| 4,992,963 | A | 2/1991 | Funt et al. |
| 5,185,850 | A | 2/1993 | Usui et al. |
| 5,315,513 | A | 5/1994 | Abreu et al. |
| 5,351,079 | A | 9/1994 | Usui |
| 5,907,629 | A | 5/1999 | Funt et al. |
| 6,038,339 | A | 3/2000 | Hubel et al. |
| 6,573,856 | B1 | 6/2003 | Obenshain |
| 6,677,885 | B1 | 1/2004 | Frankot |
| 6,834,125 | B2 | 12/2004 | Woodell et al. |
| 6,909,815 | B2 | 6/2005 | Berstein et al. |
| 7,583,863 | B2 * | 9/2009 | Fouquet et al. ............ 382/312 |
| 2004/0153284 | A1 | 8/2004 | Bernstein et al. |

OTHER PUBLICATIONS

Finalyson, G.D. et al, "Color Constancy at a Pixel", Journal of Optical Society of America, vol. 18, No. 2, 2001, pp. 253-264.

Finalyson, G.D. et al., "Removing Shadows from Images", Computer Vision, ECCV 2002, Part IV, pp. 1-14.

Kruse, F.A. et al, "The Spectral Image Processing System (SIPS)—Interactive Visualization . . . ", Remote Sensing of Environment, vol. 44, 1993, pp. 145-163.

Benedicktsson, J.A. et al., "Neural Network Approaches versus Statistical Methods of Classification . . . ",IEEE, Trans. Geosci, and Remote Sensing, vol. 28, 1992, pp. 540-552.

Adler-Golden, S.M. et al.,"Shadow-Insensitive Material Detection/Classification with Atomspherically Corrected Hyper-Spectral Imagery", Proc, SPIE, vol. 4381, 2001, pp. 460-.

"Spectral Gradients for Color-Based Object Recognition and Indexing", Berwick, D. et al., Computer Vision and Image Understanding, vol. 94, 2004, pp. 28-43.

* cited by examiner

METHOD FOR SPECTRAL DATA CLASSIFICATION AND DETECTION IN DIVERSE LIGHTING CONDITIONS

CROSS REFERENCES TO RELATED APPLICATIONS

This application claims priority to U.S. Application No. 60/774,057 filed on Feb. 16, 2006.

STATEMENT REGARDING FEDERALLY SPONSORED RESEARCH

Not Applicable.

BACKGROUND OF THE INVENTION

Field of the Invention

This invention is a method for the classification of spectral data such as multi-spectral or hyper-spectral image pixel values or spectrally filtered sensor data. The spectral data classification method enables operator supervised and automated target detection by sensing spectral characteristics of the target in diverse lighting conditions. The method can be applied to sensing and imaging for homeland security, defense, environmental protection, biomedical diagnostics, and for industrial process and product monitoring.

Measurement of the spectral reflectance of an object, or the absorption, or transmission of light passing through an object or medium requires knowledge of the spectral content of the incident light used for illumination. The signal of a spectrally-resolving sensor depends on: (a) the spectral content of the illumination; (b) the spectral sensitivity of the sensor; and, (c) the spectral properties of the object, i.e., its spectral reflectance, absorptance, or transmission. As an example, a hyper-spectral or multispectral camera records the data in each spectral band as a radiance map of a scene. Therefore, for viewing an object or scene in reflected (or transmitted) light, a pixel value depends on the spectral content of the incident light, spectral sensitivity of the camera, and the spectral reflectance (or transmittance) of the target. For many sensing applications, e.g., for target detection, recognition, or characterization, it is the spectral reflectance of the target that is of interest and not the characteristics of the sensor or the illumination. This is also the case for photometric applications such as color matching by spectral reflectance comparison and material identification or characterization by spectral absorption and transmission methods. To convert spectral radiance into spectral reflectance, absorptance, or transmittance, some kind of radiometric correction must be performed for all existing methods (see, for example, T. H. Lillesand, R. W. Kiefer, J. W. Chipman, Remote Sensing and Image Interpretation, Fifth Edition, Chapter 7, John Wiley & Sons, New York, 2004).

The conversion from radiance map to spectral characteristics of the scene or objects within a scene, e.g., reflectance, absorptance, or transmittance, is essential for accurate pixel classification for target detection, photometric analysis, and object identification, recognition, characterization, or tracking.

Correction for the spectral sensitivity of a camera is a simple operation. Calibration is performed by recording an image cube of a light source with known spectrum, e.g., an etalon light source, and comparing the experimental data with the tabulated known spectrum. In practice, the transfer function of the camera often is obtained as a pixel-by-pixel determination of the ratio of measured signal and the light incident on the camera aperture for each spectral (i.e., wavelength) bin of interest.

In contrast, correction for the spectral content of the incident light on the scene and objects within the scene, i.e., the lighting or illumination, is a complicated and difficult procedure. For indoor scenes, lighting may be from natural and manmade sources. These may comprise thermal and non-thermal emitters with spectra that are modified by dynamic conditions and there may be multiple uncontrolled variables. For many imaging and sensing situations, independent or a priori knowledge of the lighting is not known. Outdoors, it is the processes of the sunlight—atmosphere interactions and dynamic phenomena, e.g., such as clouds. As it is well known, the extra-terrestrial sun spectrum can be approximated with a Planckian spectral distribution curve corresponding to the radiator temperature T=5800 K, which is shown in FIG. 1.

There are several processes changing the spectrum when sunlight travels through the atmosphere. The most important of them are:
- scattering on air molecules (Rayleigh scattering),
- scattering on aerosols and particulate (Mie scattering),
- absorption by air constituents and aerosols,
- absorption and reflection by clouds.

All of these processes are dynamic by two reasons: earth motion and changing atmospheric conditions. Earth motion results in variable sun elevation angle, which is responsible for the thickness of the atmosphere to be pierced by sunlight before it reaches the ground. The length of sunlight-atmosphere interaction is usually referred as the air mass (or atmosphere mass) m. It is the path of direct solar beam through the atmosphere, measured in the units of the minimum path, which corresponds to the sun's being directly above the measurement point (zenith angle Z=0, elevation angle E=90°). If the measurement point is above the atmosphere, i.e., for extra-terrestrial sunlight, the air mass m=0. For sea-level point and Z=0, the air mass value is m=1. In general, $m \approx 1/\cos(Z)$.

While the elevation angle and air mass values are predictable and can be calculated and taken into account by measuring time, date, and geo-positional information, the atmospheric conditions (humidity, temperature, aerosol composition and density, cloudiness, etc.), are not. In particular, the motion of clouds creates fast changing shape shadows. Additional shadowing is associated with configuration (shape and positions) of objects in a scene.

The described above factors can be divided in two groups: global and local for each considered scene. The global factors are constant over the entire scene, while the local factors depend on a position within the scene. It is much easier to compensate for global variation in lighting, than for local factors. There are numerous global and local methods for compensation of lighting change effects in the prior art.

The global radiometric calibration is a straightforward procedure and can be achieved by several generally used methods. The simplest way to calibrate a hyper-spectral system is to acquire an image cube of an object of known spectral reflectance or transmittance and use this data to calculate correction factors for each band.

A better result is given by the so-called empirical line method, which uses acquisition of an image cube with two or more targets of known reflectance and plotting a graph representing the dependence of pixel values on reflectance for each band. This method allows for calculation of two parameters for each pixel (i.e., channel) of the sensor (e.g., a camera or imager): offset and gain. Removing the offset subtracts the dark current and path radiance contributions from the signal.

An alternative to such methods uses camera calibration with known lighting conditions combined with monitoring lighting variations. This allows correction of the acquired hyper-spectral data in accordance with the observed changes. This can be performed with a separate spectrometer, which collects sunlight and skylight, or by multiplexing a hyper-spectral or multi-spectral camera between scene and light source(s) measurements.

All of the above methods are global ones and cannot correct for local lighting variations in a scene unless the variations are strictly spatial variations and are static in time. Also, they demand additional equipment such as calibration targets, a spectrometer, or multiplexing system. It is not generally possible to install adequate calibration targets in a scene. This is particularly true for outdoor sensing applications, especially for sensing from mobile or airborne platforms. It is also true for volatile indoor scenes that contain moving or changing objects. Also, finding the calibration targets is difficult and may not be reliable in acquired image cubes in an automated mode without the participation of a human operator.

A more sophisticated method of image calibration, including a type of local correction, namely deshadowing, is described in S. M. Adler-Golden, R. Y. Levine, M. W. Matthew, S. R. Richtsmeier, L. S. Bernstein, J. Gruninger, G. Felde, M. Hoke, G. Anderson, and A. Ratkowski, "Shadow-insensitive material detection/classification with atmospherically corrected hyper-spectral imagery", *Proc. SPIE*, 4381, pp. 460-469, (2001). The approach includes atmospheric correction of the data to generate apparent surface spectral reflectance, calculating a skylighted-to-fully-illuminated spectral ratio, applying the ratio to a fully-illuminated reflectance spectrum of a chosen material, and incorporating both the original and the shadowed spectrum in a detection or classification algorithm. The classification algorithms are generalized to accommodate the sky-versus-sun spectral difference by representing the desired target reflectance as a linear combination of the skylighted spectral signature and the direct sun-illuminated signature (the latter is the difference between the fully-illuminated spectral signature and the skylighted signature). If the sky is considered as a spectrally-uniform source, then all combinations of sky and sun illumination can be presented by some positive linear combination of those two spectra, even when there is less than full sky illumination. With this approach, the authors demonstrated significant improvement for shadowed objects. However, this approach is computationally intensive and, at present, can be done only in post-processing of hyper-spectral data. In addition, operator assistance is required, so real-time, automated target detection is not feasible with this method.

Another method for local compensation of lighting effects in hyper-spectral data is proposed in US Patent Application Publication No. 2004/0153284 by L. S. Bernstein, S. M. Adler-Golden, T. M. Perkins, A. Berk, R. Y. Levine, "Method for performing automated in-scene based atmospheric compensation for multi and hyper-spectral imaging sensors in the solar reflective spectral region", filed Jan. 31, 2003. It provides automatic compensation for atmospheric effects by resolving plurality of spectrally diverse pixels from an image cube, determining a spectral baseline from the spectrally diverse pixels, determining a statistical spectral deviation of the spectrally diverse pixels, normalizing the statistical spectral deviation by applying a scale factor, and compensating image pixels with both spectral baseline and the normalized spectral deviation. As Bernstein et al. teach, the method allows for reasonably accurate radiance conversion into reflectance without knowing the spectral content of illumination. There are three main assumptions in the approach of this invention:

1) There are ten or more diverse pixel spectra in the scene;
2) The spectral standard deviation of reflectance for diverse materials is wavelength independent; and
3) There are sufficiently dark pixels in a scene to allow for a good estimation of the baseline contribution.

In the model, sun-surface-sensor atmospheric transmittance loss is a factor multiplying the true reflectance while the cross talk component resulting from atmospheric scattering and the light scattered and absorbed by the atmosphere are additive constants. The key underlying assumptions of the authors' approach are (1) several spectrally-different end-member pixels can be extracted from the data, and (2) the true spectral standard deviation for a (spectrally) diverse set of pixels is a constant. Then, it follows from their model that the standard deviation of the acquired image cube itself becomes an estimate of the atmospheric transmittance loss factor, within (unknown) scale factor. The acquired-image cube is than first compensated by subtracting an estimate of the baseline offset (i.e. the two additive components), which is determined from the dark pixels in the image, followed by the correction for atmospheric transmittance loss.

Bernstein et al. offer several ad hoc methods and guidelines for a number of necessary elements of the approach such as how to estimate endmembers, the baseline correction, and the scale factor for normalizing standard deviation (which depends on whether sensor measurements are calibrated or not). While the overall method appears to be possible to automate, it is not clear how the different approximations affect the accuracy of the method and the execution speed. Although useful for local correction, this method includes several assumptions and empirical factors, and by these reasons, it is not universally applicable. Also, the accuracy of radiance conversion into reflectance with this method is questionable.

Classification of hyper-spectral images and target detection are usually done in the feature space, which is an N-dimensional space with spectral reflectance axes. Each pixel of a scene image is represented by an N-dimensional vector in this space. Usually, two-dimensional projections on planes with axes Ri, Rj are deployed to display results. Known methods of target detection include Euclidean and Mahalanobis distance measurement, Spectral Angle Mapper, and artificial neural networks.

Distance-based methods of classification and detection are the most obvious and simple. They compare template spectral signatures from previously taken lab or ground truth measurements with spectral signatures of all pixels in the image cubes under classification. The Euclidian distance is calculated as the square root from the sum of squares of differences between the spectra in all spectral bands. The Mahalanobis distance calculations are corrected for covariance of the data for each band. After these calculations, the pixels are sorted with sorting based on a threshold, i.e., all pixels closer than the threshold are classified as belonging to the class and the rest pixels are considered as members of other classes.

Spectral Angle Mapper (SAM) is an automated method for comparing image spectra to individual spectra or a spectral library (Kruse, F. A., Lefkoff, A. B., Boardman, J. W., Heidebrecht, K. B., Shapiro, A. T., Barloon, J. P., and Goetz, A. F. H., The spectral image processing system (SIPS)—Interactive visualization and analysis of imaging spectrometer data: *Remote Sensing of Environment*, v. 44, p. 145-163 (1993)). The algorithm determines the similarity between two spectra by calculating the "spectral angle" between them, treating them as vectors in a space with dimensionality equal to the number of bands N. Graphically, this may be depicted as vector projections on multiple planes, for each of which the coordinate axes are reflectivities in the spectral bands i and j ($1<i, j<N+1$; $i \neq j$). Because only the direction of the spectral vectors is used and not their length, the method is insensitive to the unknown gain factor, and all possible illuminations are treated equally. Poorly illuminated pixels will fall closer to the origin. The material color is defined by the direction of its unit vector. The angle between the vectors is the same regardless of the length, while the latter relates only to illumination intensity. There are multiple projections of N-dimensional spectral vector, associated with each pixel, where N is the number of spectral bands. By measuring angle in the N-dimensional feature space SAM classifies all pixels as belonging or not to each given class. Spectral angles are determined for spectral vectors, corresponding to each pixel. This value is assigned to the corresponding pixel in the output SAM image, one output image for each reference spectrum. The derived spectral angle maps form a new data cube with the number of bands equal to the number of reference spectra used in the mapping. Thresholding is typically used to determine those areas that most closely match the reference spectrum. SAM calculates the angular distance between the spectral vector for each pixel in the image and the reference spectra or end-members in N-dimensions. The result is a classification image showing the best SAM match at each pixel.

Artificial neural networks (NN) currently find broad application in hyper-spectral imaging for classification and target detection. They represent a non-deterministic approach to hyper-spectral classification. The advantages of neural network (NN) based approaches for classifying hyper-spectral images have been recognized for a while (see, for example, J. A. Bendicktsson, P. H. Swain, O. K. Ersoy, "Neural network approaches versus statistical methods of classification of multisource remote sensing data", *IEEE Trans. Geosci. and Remote Sensing*, 28, 540 (1992)). NNs are considered to be powerful classification tools because of their nonlinear properties and the fact that they make no assumptions about the distribution of the data. This feature is useful in cases where no simple phenomenological model exists to accurately describe the underlying physical process that determines the data distribution. The NN system must be trained before use. During training an operator inserts multiple samples of various classes and allows the NN to acquire proper knowledge about a scene and objects/subjects, included in it. As the result, the NN system generates internal criteria to be used in future image classification. The NN classification is flexible and precise, but demands human-assisted training and works slower than SAM and other deterministic algorithms.

A neural network consists of three or more layers: an input layer, an output layer, and one or more hidden layers. Each layer is made up of multiple nodes, which are referred sometimes as neurons. The nodes in the input layer represent variables used as input to the network: spectral bands from an image cube, textural features, derived from the image cube, or ancillary data describing the region of interest. The output layer nodes represent the range of possible output categories to be produced by the network. There is one output for each class in the classification system. The hidden layers consist of multiple nodes, each linked many nodes in the input and output layers. The linkages have their weights, which guide the flow of information through the network. The network gets tuned to solution of a specific problem during training, when an operator inserts samples of classes to be found by the network later. Increase in the amount of hidden layers permits more complex analysis at expense of lower generalization and longer training process. A neural network is not guaranteed to find the best solution of a classification task, because it can be caught in a local minimum rather than reaching the absolute minimum error. Alternatively it can get into oscillation between slightly different states, forming a non-converging or poorly converging loop or process.

Each of these methods has proven to be useful for certain situations, but each has disadvantages. The principal disadvantage is that they all require calibration for the conversion of target spectral radiance into its spectral reflection, and as lighting conditions change, the calibration must be updated. Basically each image cube must have its own calibration to account for changing illumination. Continuous calibration is not always possible, especially if a hyper-spectral system must work in an autonomous mode or if it is moving, and analyzed scenes change accordingly and not predictably.

In addition, all of these methods are problematic with low brightness targets. Typically, problems arise with targets in poor illumination or those of low reflectance. The problems are associated with the fact that dark pixels group near the origin in the feature space and are not distinguishable by their colors.

When light sources can be described by a known analytical formula, it is possible, in some cases, to find a transform for decoupling target chromaticity and light chromaticity. After such a transform, a target spectral signature does not depend on the spectral contents of the incident light and by this reason no field calibration is required for target detection in diverse lighting conditions. Such a decoupling transform applies provided all light sources belong to the same class and can be described by the same formula, although the parameter values in the formula may vary within some limits.

This approach was used in G. D. Finlayson and S. D. Hordley, "Color constancy at a pixel", Journal of the Optical Society of America, Vol. 18, No. 2, pp. 253-264 (2001), to find a color invariant in images taken by color cameras that have three broad spectral bands: red (R), green (G), and blue (B), and so N=3. Finlayson et al. use a transform to a delta-logarithmic feature space wherein the pixel values $P_R$, $P_G$, $P_B$, for the R, G, B color bands are mapped as the logarithms of ratios of pixel values, e.g., $\ln(P_R/P_G)$ vs $\ln(P_B/P_G)$. An isochrome is the curve in feature space that is fitted to the points representing a given color target at several light source color temperatures. In another publication (G. D. Finlayson, S. D. Hordley, M. S. Drew, "Removing shadows from images", Computer Vision-ECCV 2002, Proceedings of the 7th European Conference on Computer Vision, Copenhagen, Denmark, May 28-31, 2002, Part IV, Springer-Verlag GmbH, ISSN: 0302-9743, pp. 823-836, 2002), Finlayson et al. showed the feasibility of de-shadowing color images with the same approach.

Although the approach of Finlayson et al. is interesting, powerful, and instructive, the method of Finlayson et al. cannot be directly applied to pixel classification or target detection in hyper-spectral/multispectral images, which have the essential characteristic of comprising maps of numerous and narrow spectral bands. The reason for the inapplicability of Finlayson et al. is that with increasing the number of spectral bands, e.g., N>>3, as in hyper-spectral or multi-spectral sensing, the spectral resolution gets better, and the method becomes more sensitive than just the three band (red, green, and blue, N=3) approach of Finlayson et al. to deviations of real light sources spectra from the ideal Planckian (i.e., Planck distribution) shape.

In fact, the inventors have determined that hyper-spectral sensing with real light sources requires analysis of the data, specifically the optimization of spectral bands and their combinations used for pixel classification or detection to best preserve the individuality and distinctness of the isochromes as is described in the present invention. As all light sources of interest have some deviations from an ideal Planckian radiator, these measures become crucially important for extending the "delta-log" approach into multi- or hyperspectral space with N>>3. Furthermore, when N=3, as in Finlayson et al., there are three delta-logarthmic feature space isochrome maps, e.g., planes based on triplets of bands that can be constructed from the three bands (with the assumption that interchange of ordinate and abscissa corresponds to an isochrome map with the same spectral information). In contrast, the number of such feature space isochrome maps for the case in which N>>3 is very much greater, namely, one-half the number of variations $$_nV_N = \frac{N!}{2(N-n)!},$$

where n=3 for triplets of bands and n=4 for quadruplets of bands. The feature space comprising the set of such isochrome maps has a much greater dimension for multi-spectral or hyperspectral sensing for which N>>3. Consequently, the inventors have concluded that the approach of Finlayson et al. is not applicable for pixel classification and target detection in such a high dimensional feature space.

There is a need for a more broadly applicable method of target detection or pixel classification, which does not require frequent calibration or calibration in the field, and which is applicable to automated real-time monitoring or real-time detection of targets of interest. The present invention addresses the need for a method to identify and select which band combinations provide the most readily distinguishable isochromes in the delta-logarithmic feature space and are useful for target detection, recognition, identification, or characterization. The method employs optimization selection criteria to accomplish this.

SUMMARY OF THE INVENTION

This specification describes a method for the classification of spectral data such as multi-spectral or hyper-spectral image pixel values or spectrally-filtered sensor data. Such data may be obtained by sensing with a digital camera that views a scene through a tunable filter. The data may also be obtained by a scanning spectrometer and a digital camera or other sensing instrument for sensing and recording image hypercube data. The light sensed from the observed scene may be light that has been reflected from the objects in the scene. It may also be light that has passed through the objects in the scene, i.e., transmitted light.

The method can be applied to the determination of chromaticity of a known target for the purpose of identifying useful detection parameters associated with such targets, or it may be used to determine the chromaticity for a presumptive target in multi-spectral or hyperspectral sensor data. If both target chromaticity and presumptive target chromaticity are known, then they can be compared to determine if the presumptive target is an actual target, i.e., the known target chromaticity can be used as a set of detection parameters or discriminants. Similarly, if most objects in a scene can be matched to a set of known objects or materials, then, anomalies in the scene can be detected.

The method uses one to several transforms of multi-spectral or hyper-spectral data to decouple target chromaticity from lighting chromaticity and the determination of a ranked set of wavelength band combinations that are sorted and ranked by merit function values so that detection parameters based on chromaticity can be determined in a subset of band combinations that comprises a few of the highest ranked band combinations. The merit function values are calculated according to one or more selection criteria that are applied to isochromes. In a preferred embodiment, the merit function values are calculated as a combination of three or more selection criteria, and so are named herein, a Tri-Criteria or Multi-Criteria sorting. In a more preferred embodiment, the merit function values are computed as a linear combination of the rankings for each of the selection criteria.

Decoupling of the presumptive or known target chromaticity and the lighting chromaticity is achieved in the delta-logarithmic feature space, where the coordinate axes are logarithms of pixel value ratios for a triplet or quadruplet of wavelengths. A rotation transform allows characteristic vectors that span a space of light chromaticity and target chromaticity as orthogonal bases. The vectors can be graphically displayed on a plot in which the horizontal axis is the measure of target chromaticity, while the vertical axis is a measure of light chromaticity. In a preferred embodiment, the measure of light chromaticity may be the effective color temperature of a light source, such color temperature preferably being based on a Planckian or near-Planckian spectral distribution.

After these transforms, pixel classification or target detection for any lighting condition is achieved by comparison of the set of pixel chromaticity values against the target discriminant parameters, which are one or more specific intervals (bands) of the horizontal coordinates that contain one or more target isochromes, i.e., the measure of target chromaticity that comprises a target signature.

Selection of the optimum combinations of spectral bands is performed by calculating a merit function, which is compiled from the rank of one or more criteria, and sorting the chromaticity data based on the merit function values. In a preferred embodiment, three selection criteria are used. The selection criteria are (1) the minimum value of the mean error of linear fitting the isochromes, (2) the isochrome parallelism to each other as the minimum difference in the angles of tilt (arc-tangent of slope), and (3) a measure that the distance between adjacent isochromes is greater than the dispersion of the corresponding classes to avoid overlap. Other criteria may include the observable presence of known target isochromes based on a priori knowledge of target chromaticity or they may include a priori knowledge of a set of known or common object chromaticities so that scene anomalies can be detected as the complement of known chromaticities.

The invention is a spectral data classification method, which enables operator supervised detection and automated target detection by sensing spectral characteristics of the target in diverse lighting conditions. The method can be applied to sensing and imaging for homeland security, defense, environmental protection, biomedical diagnostics, and for industrial process and product monitoring.

The invention determines the spectral reflectance of an object, or the absorptance, or transmission of light passing through an object or medium based on a Planckian or near-Planckian spectral distribution of the incident light used for illumination. The absorptance is obtained by sensing both the light reflected from objects on their illuminated side and the light transmitted through the objects, and subtracting reflected and transmitted light from the incident illumination. This method is applicable particularly to thin targets or targets for which internal scattering or adjacency effects are negligible.

This invention may achieve one or more of the following:
1) reliable target detection or image pixel classification under diverse and variable lighting conditions;
2) a substantial reduction in the frequency or elimination of the need for periodic or frequent calibration of a hyper-spectral or multi-spectral camera, such calibration being made to compensate for changes in the spectral content of illumination;
3) a sufficiently rapid method of pixel spectral classification to enable automated target detection in real time, a key feature being the sorting and identification of optimized combinations of spectral bands for pixel classification and discrimination of target spectral characteristics;
4) a rapid method of sorting chromaticity data to enable operator supervised selection or refinement of target chromaticity-based discriminants for target detection, identification, recognition, or characterization;
5) a rapid method of sorting chromaticity data to enable detection of objects with known chromaticities in a scene so that the complement that corresponds to an anomaly can be detected; and
6) better detection of "dark" (i.e., poorly illuminated) targets or the classification of "dark" pixels, e.g., by the use of the delta-logarithmic space decoupling, and so, to also obtain the extension of useful camera dynamic range.

The method is well suited to pixel classification or target detection by means of spectral image analysis for scenes with diverse or dynamic lighting conditions. Beyond existing methods such as SAM and other commonly employed methods, the method described in this specification extends the concept of decoupling target and light chromaticities into a multi-dimensional hyper-spectral feature space for hyper-spectral and multi-spectral imaging, pixel classification, and target detection.

The method uses the decoupling of presumed-target chromaticity and lighting chromaticity in the delta-logarithmic feature space and an invariant set of detection or classification parameters.

The method comprises the steps of:

Acquiring at least two sets of multi-spectral or hyperspectral image data, each set being an image hyper-cube for a scene and the two sets having been acquired with illumination having different chromaticity, and the additional steps of:

Performing a logarithmic transform of the acquired image hyper-cubes;

Calculating chromaticity maps for all triplets or quadruplets of wavelengths, each said triplet or quadruplet comprising a "band combination", and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space, then determining isochrome lines for each band combination, and, optionally, the resulting isochromes being rotated to a vertical orientation;

Sorting all band combinations by merit function values, the value of each band combination being calculated as a function of the value of one or more criteria that are applied to the isochromes, and the sorting being the ranking of the band combinations according to their merit function value, the greatest rank being given to the most advantageous merit function value;

Comparing presumed-target chromaticities in a subset of feature space that corresponds to one or more of the highest ranked band combinations with classification or detection discriminant parameters;

Generating a detection mask, i.e., the denotation of the subset of pixels that have been identified, i.e., classified, as having chromaticity that sufficiently matches the detection discriminant parameters, and Registering or outputting the results of detection, for example exhibiting the results as a display, or storing the results in a memory, or generating a signal such as an alarm.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 8 b-c demonstrate detection of human skin with the method of the present invention, (c: T=3100 K, d: T=1800 K).

DETAILED DESCRIPTION OF THE PREFERRED EMBODIMENTS

Figure 1:
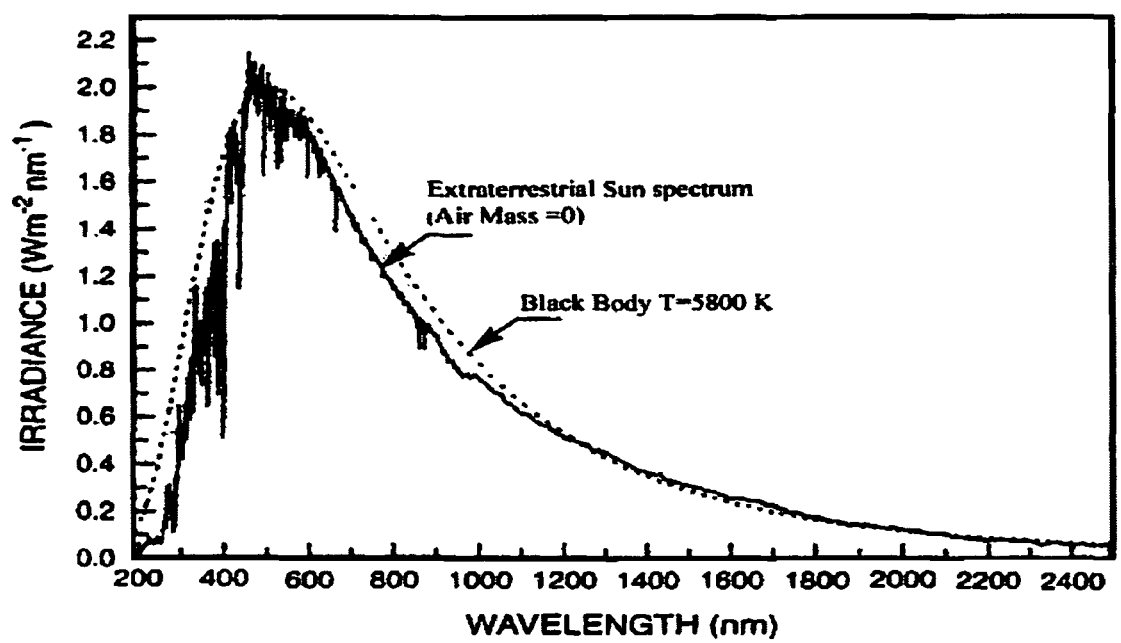
FIG. 1 is a graph of the extra-terrestrial sun spectrum compared to the Planckian black body radiator at T=5800 K.

The following description of the preferred embodiment(s) is merely exemplary in nature and is in no way intended to limit the invention, its application, or uses.

The method uses an invariant set of detection or classification parameters and the decoupling of target chromaticity and lighting chromaticity in the delta-logarithmic feature space with the sorting and selection of band combinations by use of merit function values that are determined from rankings that are made according to one or more selection criteria.

The method is used in the short wavelength regime as described below in Eqn. (3) or in the long wavelength limit, which is the limit in which $T\lambda \gg c_2$, and the parameters $T$, $\lambda$, and $c_2$ are defined below. The lighting chromaticity can be measured as a function of equivalent color temperature, which temperature is based on a Planckian or near-Planckian spectral distribution. In the long wave regime, the method applies when the thermal radiance, i.e., thermal emission from the objects in the scene, is much less than the reflected or transmitted light from the illumination source. The method also applies in the long wave regime when there is little or no illumination in comparison with the thermal emission from the objects in the scene. In this case, instead of determining reflectance or transmittance, the method can be used to determine emissivity.

The method begins with the acquisition of a multi-spectral or hyperspectral image hyper-cube. The data are then transformed. The transform (or "mapping") to delta-logarithmic space is based on the following analysis. The signal $\tilde{P}_\lambda$, recorded by a sensor pixel at wavelength $\lambda$ can be expressed as $$\tilde{P}_\lambda = E_\lambda S_\lambda R_\lambda + P_{DC}{}^\lambda + P_{PR}{}^\lambda, \quad (1)$$

where $E_\lambda$ is illumination at wavelength $\lambda$, $R_\lambda$ is the target reflectivity at wavelength $\lambda$, $S_\lambda$ is the camera response at wavelength $\lambda$, $P_{DC}{}^\lambda$ is the dark current signal, and $P_{PR}{}^\lambda$ is the path radiance signal at wavelength $\lambda$.

Note that the dark field signal does not depend on wavelength directly, but it is proportional to the integration time, which is wavelength-dependent, because in order to improve the use of the sensor dynamic range, exposures are optimized and differ significantly for bands.

Correction of the data may be performed by removing $P_{DC}{}^\lambda$ and $P_{PR}{}^\lambda$ with one of standard methods, for example, the empirical line method. This correction can be done in advance when a camera is tuned. However, dark pixel subtraction may be advantageous and preferred as it does not require calibration targets in the scene or a priori information.

In dark pixel subtraction, the average value of several darkest pixels from the same band is subtracted from the pixel signals in each spectral band. Although, this method is not as precise as the empirical line method, it is advantageous because no calibration targets are required. In many situations, it may be the only choice.

For modeling a real situation the following three simplifying assumptions are made.

1). All light sources are approximated by the Planck's formula for a black body radiator with an appropriate for a given light source color temperature T:

$$E(\lambda, T) = I \frac{c_1}{\lambda^5 \left[\exp\left(\frac{c_2}{T\lambda}\right) - 1\right]}, \quad (2)$$

where I is the scaling factor, proportional to the power of the black radiator, $c_1 = 3.74 \cdot 10^{-16}$ W·m², $c_2 = 1.44 \cdot 10^{-2}$ K·m, T is the temperature of the black body radiator in K, and $\lambda$ is the wavelength in m.

For the extraterrestrial sun radiation, the color temperature T=5800 K and the spectrum is shown in FIG. 1. At sea level T depends on the zenith angle, geo-position, aerosol component, and some other parameters. To some extent the discrepancy between the real sun spectrum and (2) can be reduced by optimization of spectral band locations and widths to avoid strong absorption bands of atmospheric gases.

2). Equation (2) can be simplified for $T\lambda \ll c_2$, because in this case (the short wavelength regime)

$$\exp\left(\frac{c_2}{T\lambda}\right) \gg 1 \quad (3)$$

and $$E(\lambda, T) \approx I c_1 \lambda^{-5} \exp\left(-\frac{c_2}{T\lambda}\right) \quad (4)$$

Note that the method can also be applied in the long wavelength limit in which $T\lambda \gg c_2$, and so, the exponential in the denominator of Eqn. 2 can be approximated as $1 + (c_2/T\lambda) + \ldots$.

3) Integration of the signal over a spectral band k yields a pixel value $\tilde{P}_k$. With the assumption of narrow spectral bands, the filtered camera spectral response can be approximated by the Dirac delta-function times a slowly varying function of wavelength $S_0(\lambda)$. Then, $$\begin{aligned} \tilde{P}_k &= \int_{\lambda_k}^{\lambda_{k+1}} E(\lambda) S(\lambda) R(\lambda) d\lambda \\ &\approx S_0(\lambda) \int_{\lambda_k}^{\lambda_{k+1}} E(\lambda) \delta(\lambda - \lambda_k) R(\lambda) d\lambda \\ &\approx E(\lambda_k) R(\lambda_k) S_0(\lambda_k) \end{aligned} \quad (5)$$

where $R_k(\lambda)$ is the target reflectance within band k, $S(\lambda) = S_0(\lambda_k)\delta(\lambda - \lambda_k)$ is the filtered camera spectral response, and $\delta(\lambda - \lambda_k)$ is the Dirac delta function. This approximation seems to be reasonable as hyper-spectral imaging deals with narrow bands. Substituting (4) into (5), we obtain:

$$P_k = \frac{\tilde{P}_k}{S_0(\lambda_k)} = I c_1 \lambda_k^{-5} \exp\left(-\frac{c_2}{T\lambda_k}\right) R(\lambda_k) \quad (6)$$

To convert the product of variables into their sum for decoupling we go to the logarithmic space:

$$\ln P_k = \ln I + \ln[R(\lambda_k) c_1 \lambda_k^{-5}] - \frac{c_2}{T\lambda_k} = \ln I + R_k - \frac{L_k}{T}, \quad (7)$$

where $R_k = \ln(R(\lambda_k) c_1 \lambda_k^5)$ and $L_k = c_2/\lambda_k$. For a specified wavelength $\lambda_k$, the first term in the right hand side of (7) depends only on the power of the light source I, the second term depends only on the target reflectance (target chromaticity), and the third term depends only on the spectral content of light (light chromaticity) as characterized by a color temperature T. This equation shows that we have decoupled the target chromaticity and the light chromaticity, and they both can be extracted from the data independently.

The light source power I can be eliminated from (7) by subtracting pixel values for two spectral bands k and l, (pre suming that I does not change during the sensing for image hyper-cube acquisition):

$$\ln P_{kl} = \ln\left[\frac{P_k}{P_l}\right] = \ln P_k - \ln P_l = R_k - R_l - \frac{L_k - L_l}{T}, \quad (8)$$

where $\ln P_{kl}$ is the logarithm of the pixel value ratio, and Eqn. (8) can be expressed in a vector form, $$P' = \Delta R - T^{-1} \Delta L, \quad (9)$$

where P' is the spectral vector for a pixel in the multidimensional delta-logarithmic feature space, $\Delta R$ is the log-chromaticity difference for the presumed or known target, and $\Delta L$ is the log-chromaticity difference for light.

Figure 2:
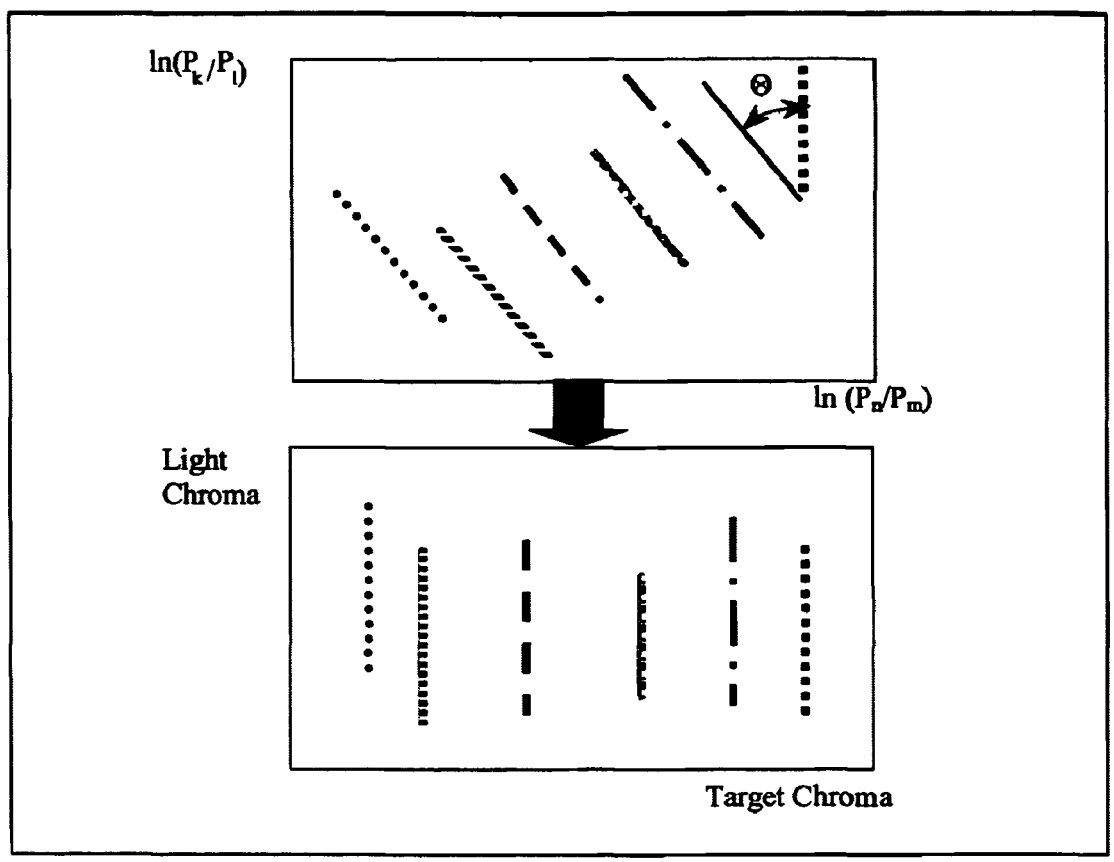
FIG. 2 illustrates two isochrome maps, one map before rotation and the other map after rotation, applied for decoupling target and light chromaticities.

The spectral vector can be presented in a standard manner by using its projections on coordinate planes that are maps of the logarithm of the pixel value ratios for the set of band combinations. Each of the planes has axes $\ln(P_k/P_l)$ and $\ln(P_n/P_m)$ as it is depicted in FIG. 2. The subscripts refer to the wavelengths ($\lambda_k, \lambda_l, \lambda_n, \lambda_m$) in a quadruplet. When $\lambda_l = \lambda_m$, the three band combination is referred to as a triplet.

In an ideal case, all lines representing different colors (isochromes) are straight and parallel to each other with significant offsets, which make detection independent upon illumination. To detect a target one needs to determine the intervals of target chromaticity values for several projections, i.e., band combinations, similar to the projection shown in FIG. 2. In practice, the isochromes are curves. However, for narrow bandwidth bands and for a range of color temperature that is of useful extent, the curves can be approximated as lines.

It is also possible to determine the absolute spectral reflectance of a pixel footprint in the scene when the color temperature is known. In the case where $\ln(P_{kl})$ has been determined from the hyper-cube data for two different known color temperatures, then $R_k$ and $R_l$ can be determined, and the vertical axis of the isochrome map can be quantitatively related to the color temperature by Eqn. (8).

In practice, the acquisition of image hyper-cube data may comprise the steps of:
  Prior calibration of the sensing instrument by measurement of the optical system-tunable filter-camera spectral response or optical system-scanning spectrometer-camera spectral response; then
  Image hyper-cube data sensing and recording, and
  Data correction for path radiance, camera signal offsets, camera dark current, and scaling of the data to obtain the scaled pixel values for the set of wavelength bands.

Once the instrument is calibrated, the method can be used to determine target signature, i.e., the classification or detection discriminant parameters, and then it can be used for target detection. The target may be an object (or material) or set of objects (or materials) in a scene. Using the method to determine target signature comprises the steps of:
  Acquisition of two or more sets of image hyper-cube data of one or more scenes, each containing the target or material of interest, the data sets differing by their illumination, which has different light chromaticity for the different data sets;
  Performing a logarithmic transform of the said acquired image hyper-cubes, the result are hyper-cubes with each element being the logarithm of the corresponding pixel value;
  Calculating chromaticity maps for all triplets or quadruplets of wavelengths, each said triplet or quadruplet comprising a "band combination", and each element of the map corresponding to a pixel, or group of pixels, i.e., a region of interest, treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space as in Eqn. (8), then determining isochrome lines for each band combination, and, optionally, the resulting isochromes being rotated to a vertical orientation;
  Sorting all band combinations by merit function values, the value of each band combination being calculated as a function of the value of one or more criteria that are applied to the isochromes, and the sorting being the ordering of the band combinations according to their merit function value, the greatest rank being given to the most advantageous merit function value; and
  Selecting a set containing one or more of the highest ranked band combinations, this set corresponding to a set of projection planes of a subspace of feature space, and identifying one or more isochromes in the subspace of feature space, and the identified isochromes and band combinations comprising the target signature.

Because of the light chromaticity diversity of the image hyper-cube data sets, isochromes in the feature space plane for a specific band combination can be determined by fitting a line to the set of centroids of a region of interest for the various illumination conditions, i.e., the different light chromaticity values. The region of interest may correspond to a specified color or known target object or material. In general, because of noise and diversity in target characteristics, a set of pixels featuring a specific color or target material will correspond to a "blob" on the chromaticity map. The position of the "blob" will shift as light chromaticity of the illumination varies. Fitting a line to the set of "blob" centroids will establish the corresponding isochrome. The set of isochromes for a scene in the feature space projection of a specific band combination is called an isochrome map (see FIG. 2). By determining the slope of the line, a rotation transform by an angle equal to "minus the arc-cotangent of the slope" can be applied to obtain nearly vertical isochromes.

The color temperature difference of the two image hyper-cube data sets used to determine the isochrome maps must be sufficiently large so that the positions of the chromaticity map "blob" centroid points are sufficiently separated so that the line fit by which the isochrome is determined has sufficient precision. The amount of separation depends on the precision of the hyper-cube data, the signal-to-noise ratio, and the extent of the "blob" in the chromaticity map. In a preferred embodiment, the extreme separation for a set of "blob" centroids for a specific isochrome is greater than the sum of the mean radii of the extreme "blobs". This condition also results in a reasonably accurate determination of the slope so that the tilt angle can be determined for a subsequent rotation transform.

In a preferred embodiment, the sorting by merit function values is according to Tri-Criteria or Multi-Criteria evaluation. The several criteria are applied to the isochromes to determine which isochromes and in which band combinations are found good classification or detection discriminant parameters.

The optimum number of highest ranked band combinations to use for the target signature can be determined by testing the image hyper-cube data sets for detection of known target pixels. In this test, a region of interest consisting of many pixels is analyzed, and the number of band combinations is varied, and for each specified number of bands, the following steps are performed:

Comparison of presumed-target chromaticities in a subspace of feature space that corresponds to the specified number of the highest ranked band combinations with classification or detection discriminant parameters that represent a known target, material or object and their known isochromes;

Detection mask generation, i.e., the denotation of the subset of pixels that have been identified as having chromaticity that sufficiently matches the classification or detection discriminant parameters, and Scoring the accuracy with which target pixels in the region of interest are classified.

Typically, it is found that a few bands provide adequate target signature. As the number of band combinations increases beyond a few, the additional advantage for each additional band combination may be very small or it may be disadvantageous.

An advantage of the present invention is that calibration of the sensing instrument, e.g., the optical system, tunable filter, and camera or the optical system, scanning spectrometer, and camera, must be done only once, provided that the results are stored with the multi-spectral hyper-spectral camera or its data processor for performing the calibration step in image hyper-cube acquisition. No recalibration in the field is required, typically.

Figure 3:
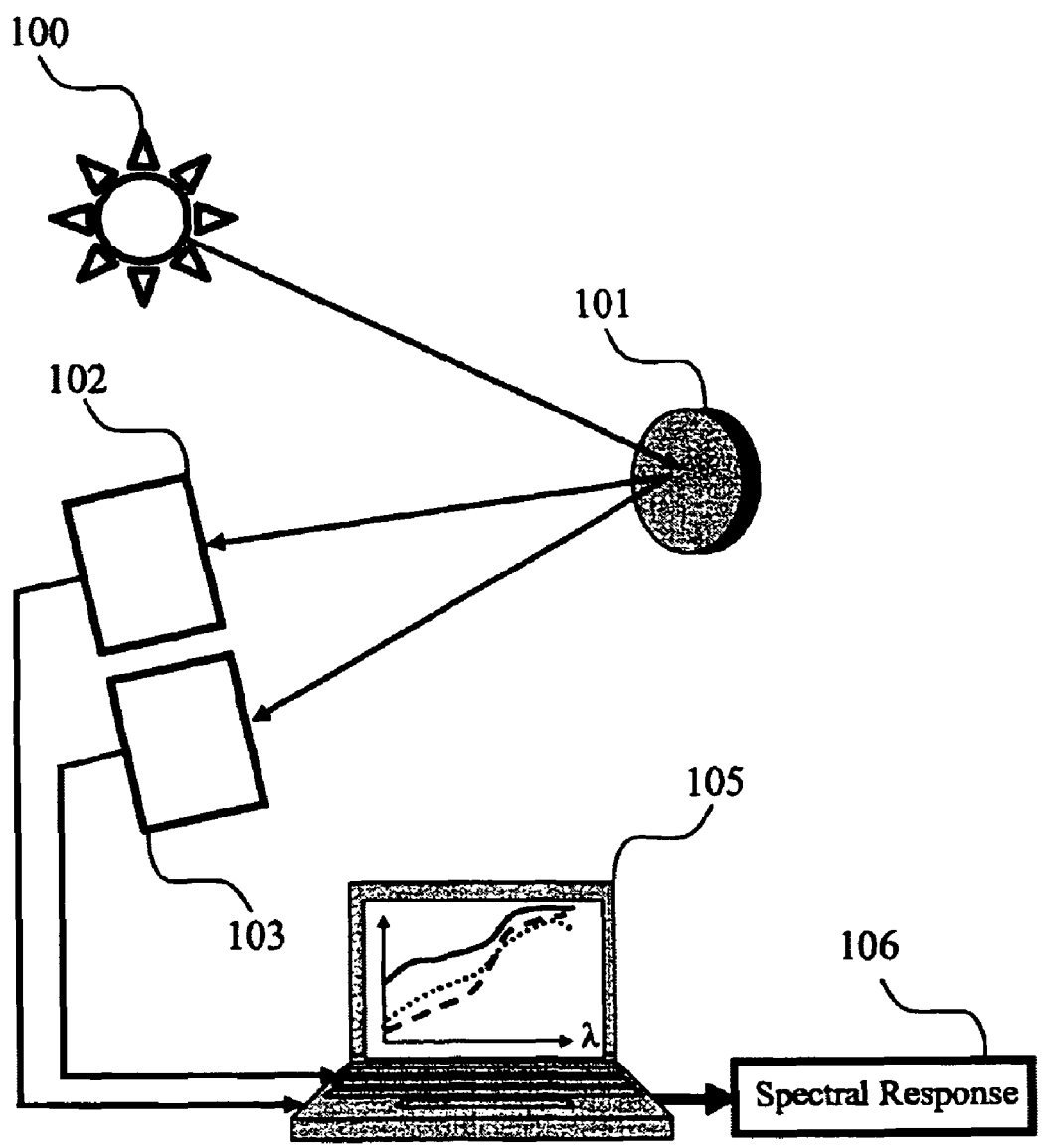
FIG. 3 illustrates a system for measuring the spectral response of a hyper-spectral camera.

Sensing instrument spectral calibration is performed for each pixel. A pixel-by-pixel spectral response curve can be generated by recording and comparison of the spectral reflectance of a specific object in the same illumination conditions with a calibrated spectrometer and the hyper-spectral camera. In principle, any object can be used for the purpose, but it is simpler to do it with a flat spectral response (gray) target as it is shown in FIG. 3. A light source 100 illuminates the calibration target 101. A calibrated spectrometer 102 and the hyper-spectral camera 103 look at the calibration target and under calibration acquire the data, which are processed by a computer 105. The output of this operation is the spectra response 106, which is stored in association with the given camera to be used in processing the data from that camera.

The spectral response generation procedure includes 3 operations:

1) Data acquisition (by using items 100-103 in FIG. 3);

2) Data processing (by 105):
    2.1. Normalization of the spectral signatures measured by the both instruments,
    2.2. Matching spectral resolutions of the deployed instruments by applying a convolution transform,
    2.3. Calculating the ratio of the spectral signatures to obtain correction coefficients for each hyper-spectral band.

3) Generation of the spectral response file 106.

It may be expected that the spectral response will remain constant until some hardware changes have occurred.

A modified version of the method can be used so that the sorting of band combinations and selection of the subset of band combinations and detection discriminant parameters need only be done once for a particular target, material, or object. This version of the method can be used when the observation conditions do not depart excessively from the conditions in which the detection discriminant parameters are determined. In this case, the method comprises the steps of:

Acquisition of image hyper-cube data and data correction as described above for a known target, material, object, or color calibration chart in various lighting conditions that correspond to various color temperature;

Performing a logarithmic transform of the acquired image hyper-cube data, the result is a hyper-cube with each element being the logarithm of the corresponding pixel value;

Calculating chromaticity maps for all triplets or quadruplets of wavelengths, each said triplet or quadruplet comprising a "band combination", and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space as in Eqn. (8), and, optionally, the resulting isochromes being rotated to a vertical orientation;

Sorting all band combinations by merit function values, the value of each band combination being calculated as a function of the value of one or more criteria that are applied to the isochromes, and the sorting being the ordering of the band combinations according to their merit function value, the greatest rank being given to the most advantageous merit function value;

Selection of a subset comprising one or more of the highest ranked band combinations, which define a feature subspace, and storage of these bands in a feature subspace band combination list and also storage of classification or detection discriminant parameters comprising the target isochromes (i.e., chromaticity) and their spacing from neighboring non-target isochromes in the feature subspace of these band combinations;

Acquisition of image hyper-cube data and data correction for a scene that is to be searched for targets, specific materials, or specific objects, this scene being referred to as a "search scene";

Performing a logarithmic transform of the acquired image hyper-cube data of the search scene;

Calculating chromaticity maps for the feature subspace, i.e., for the subset of band combinations selected above, and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space as in Eqn. (8), and if a rotational transform was applied to the isochrome map, then, applying the same rotational transform for that band combination;

Comparison of presumed-target chromaticities in the feature subspace with the above identified classification or detection discriminant parameters that represent a known target, material or object, Detection mask generation, i.e., the denotation of the subset of pixels that have been identified as having chromaticity that sufficiently matches the classification or detection discriminant parameters, and Registering or outputting the results of detection, for example exhibiting the results as a display, or storing the results in a memory, or generating a signal such as an alarm.

Several variations to the method may be useful. Target or material characteristics can also be obtained by other prior measurements or other a priori knowledge. The determination of target, material, or object chromaticity and classification or detection discriminant parameters may be determined in a controlled setting such as a laboratory or it may be obtained in a naturally varying setting. Thus, such determination may be performed indoors or outdoors. The number of band combinations selected for the feature subspace may be determined by operator supervision, or it may be determined by calculation of a detection probability for a set of test images as a function of the number of band combinations in the feature subspace. Such a procedure can be automated or it can be performed with operator supervision. In a preferred embodiment, three to six triplets are found to be adequate for most situations.

Anomaly detection may be performed by the determination of chromaticities for several known materials or objects and then detecting such in a search scene as the complement to anomalies. In an alternative approach, isolated pixels or patches of pixels may be identified as anomalies when surrounded by a larger region of different chromaticity or chromaticities in a region of interest.

Figure 4:
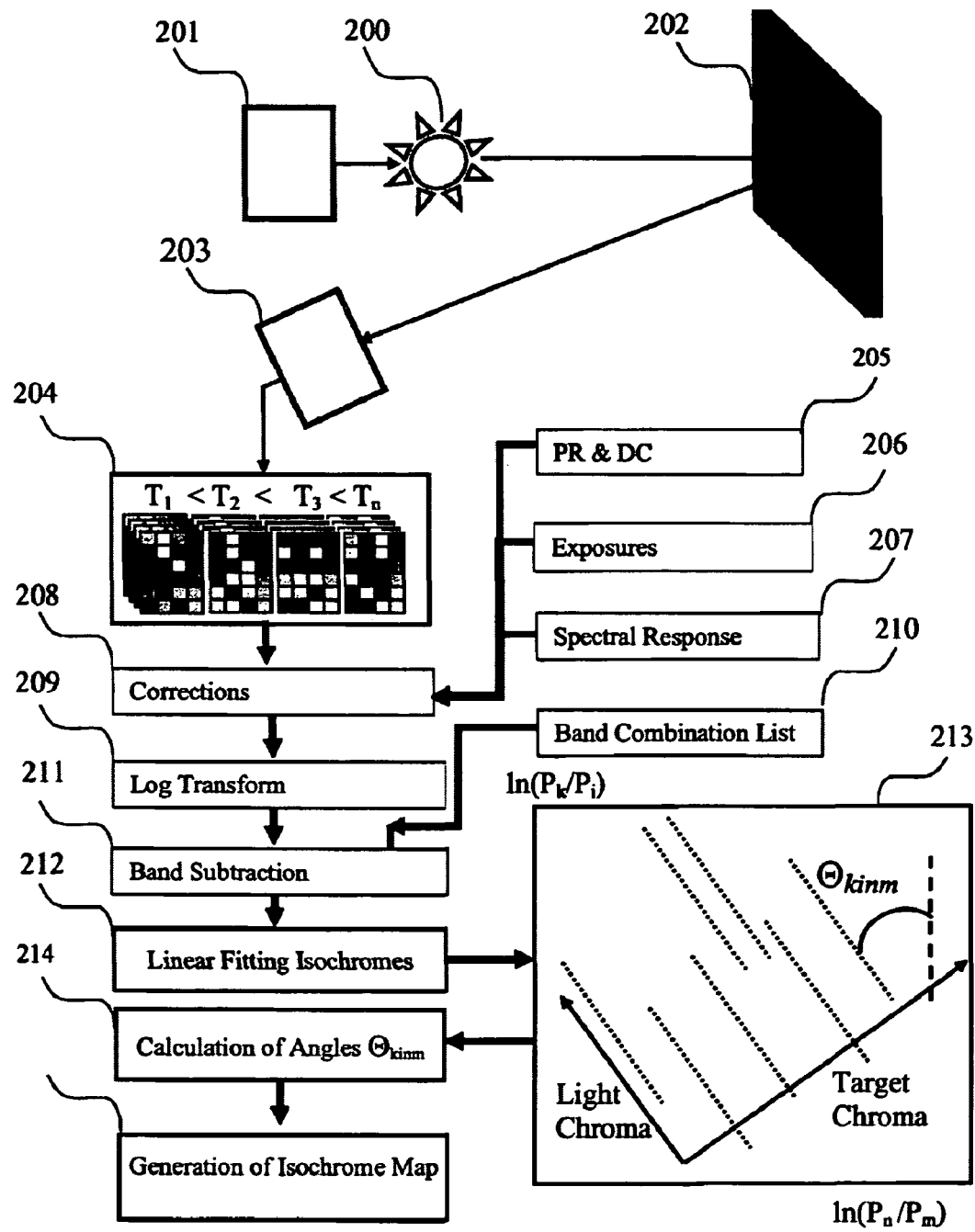
FIG. 4 illustrates an isochrome mapping flow chart.
Figure 5:
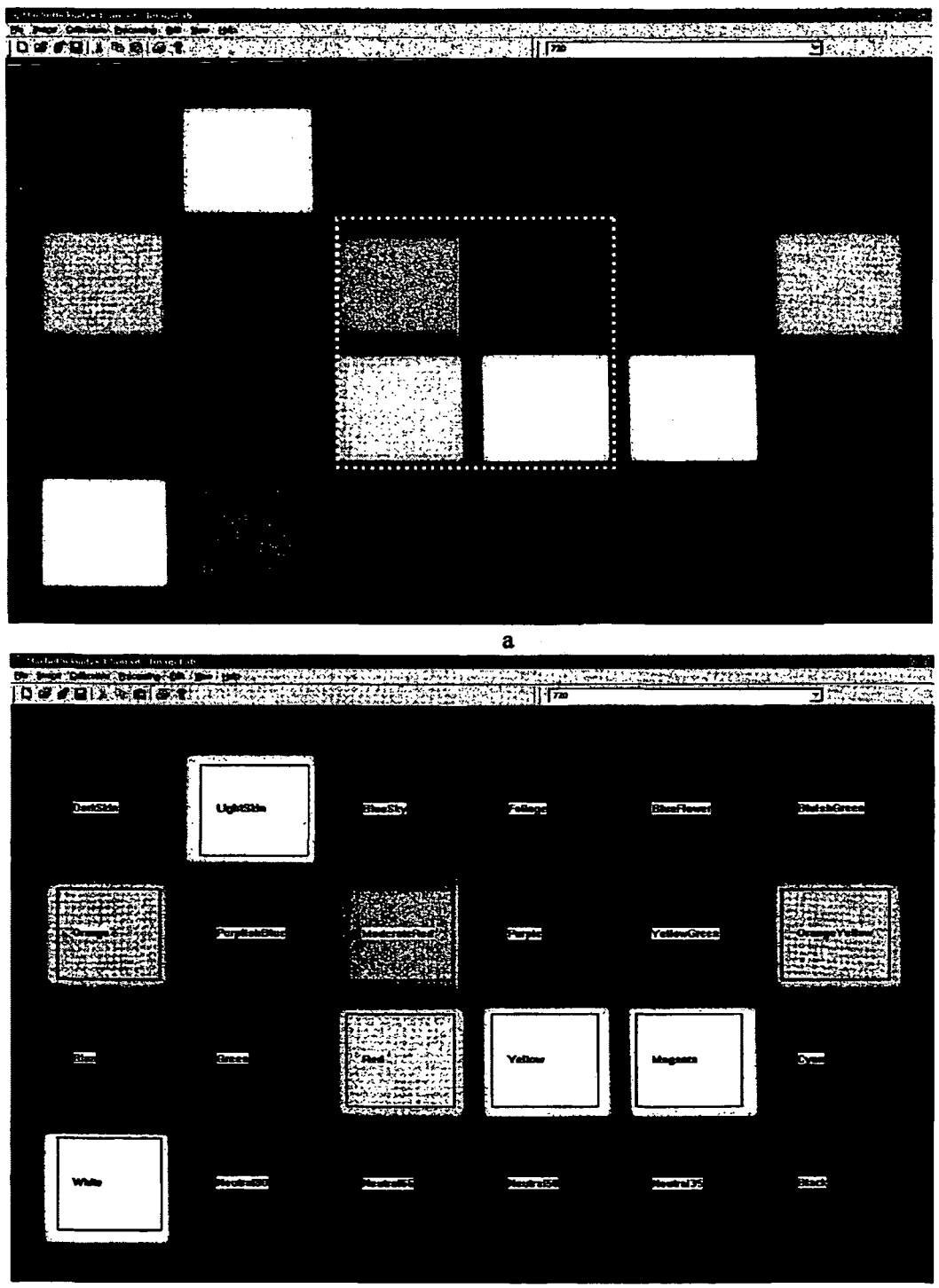
FIG. 5 is a screen shot of a Macbeth color chart software application in the process of finding color squares in order to generate isochrome maps.

Generation of isochrome maps for a color calibration chart can be performed as a means of color calibrating the sensing instrument, e.g., an optical system+tunable filter+camera. A flow chart for obtaining isochrome maps in feature space is shown in FIG. 4. Light source 200 illuminates a target 202 with multiple color sections, for example the Macbeth color checker chart (as shown in FIG. 5), including 18 color squares and 6 gray squares of various density, may be used. For this operation the light source 201 must provide a range of color temperatures. This can be implemented with supplying variable voltage to an artificial light source or by acquiring image cubes at different time during a day, when the sun position varies and variable air mass changes effective color temperature of sunlight.

Image cubes 204 are acquired with a hyper-spectral camera 203 at n color temperatures of the light source from $T_1$ to $T_n$. The next step is correction 208 of the image cubes 204. The correction includes: subtraction of the additive components—path radiance PR and dark current DC—205, normalization for exposure (integration time) 206, and correction of the spectral response 207. The corrected image cubes are subjected to the logarithm transform 209 and after that subtracted from each other 211 according to the band combination list 210. After the last operation all data are in the delta-logarithmic feature space. Each image cube gives a single point for each color and this point corresponds to light chromaticity at color temperature $T_i$. Therefore, the complete dataset from all image cubes comprises 24 isochromes (6 of them for shades of gray). According to Equation (9) the isochromes should be straight lines. Based on this expectation, the next operation is fitting the experimental points with straight lines 212. After fitting, the data looks as shown in display 213. The tilt angles Θ for all projections are calculated in 214. The last operation is generation and saving the isochrome map 215. The isochrome map file can be used as a color calibration of the sensing instrument, and can be stored with it or the computer used for data analysis.

The isochrome mapping procedure of FIG. 4 comprises 8 operations:

1) Data acquisition (items 200-204 are involved);

2) Data correction (items 205-208);

3) Logarithmic transform (item 209);

4) Band subtraction (items 210, 211);

5) Linear fitting isochromes (item 212);

6) Display of isochrome maps (item 213);

7) Calculation of rotation angles (item 214);

8) Generation of the isochrome map (item 215).

Figure 6:
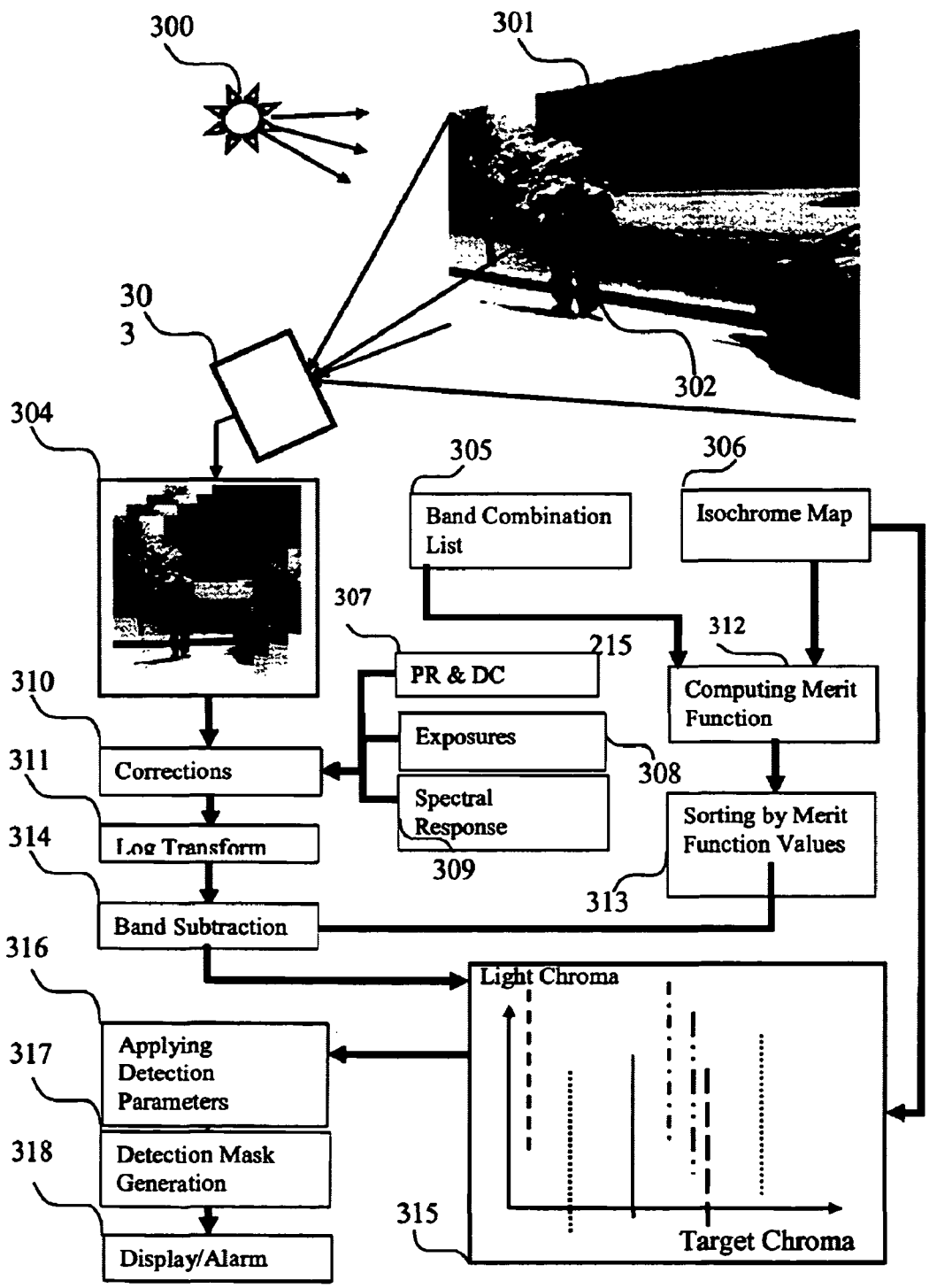
FIG. 6 illustrates a target detection flow chart.

An example of target detection is given as a flowchart in FIG. 6 and described below. The image of a scene 301, illuminated by a light source 300 and including one or more presumptive targets 302, is acquired by a hyper-spectral or multispectral sensing instrument such as an optical system+tunable filter+camera 303. Acquired image hyper-cubes 304 are processed in real time to decouple presumptive target chromaticity and light chromaticity. The processing flow includes image corrections 310 for path radiance and dark current (baseline subtraction) 307, exposure normalization 308, and spectral response 309, then, the logarithmic transform 311 is performed, chromaticity maps are generated by spectral band subtraction 314 in the logarithmic feature space, and a rotational transform 315 is applied to obtain the desired feature space maps, next, detection parameters 316 are applied, and detection mask generation 317 is performed to denote which pixels are classified as targets, finally, the process produces a data product by displaying the results and alarm generation 318 if a target is found. In a preferred embodiment, the spectral band subtraction transform is performed over a subspace of feature space that comprises a set of 3 to 6 band combinations that have been previously determined from image hyper-cube data of a known target, or known materials or objects and after such data have been transformed and isochrome maps 306 have been generated for all band combinations according to the band combination list 305, and merit function values have been computed 312, and sorted 313 to rank the band combinations. It should be noted that the isochrome map data 306 may also be used to predict the rotational transform 315.

Pixel classification and detection is accomplished by setting two limits for each isochrome for each band combination in the selected feature subspace. These limits are implemented by two vertical lines as separators of the isochrome belonging to the target class. These limits define a window in which a presumptive target must lay to be classified as a target, i.e., for the presumptive target to match the known target discriminant. When isochromes in several band combinations comprise the detection parameters that define a target signature, then a presumptive target may be scored according to how many isochromes match. For high confidence detection, 100% match may be required. However, for many situations, a lower confidence level may be acceptable for classification of individual pixels, and target detection may be based on the number of nearby pixels in a region of interest in the scene are classified as targets.

Figure 7:
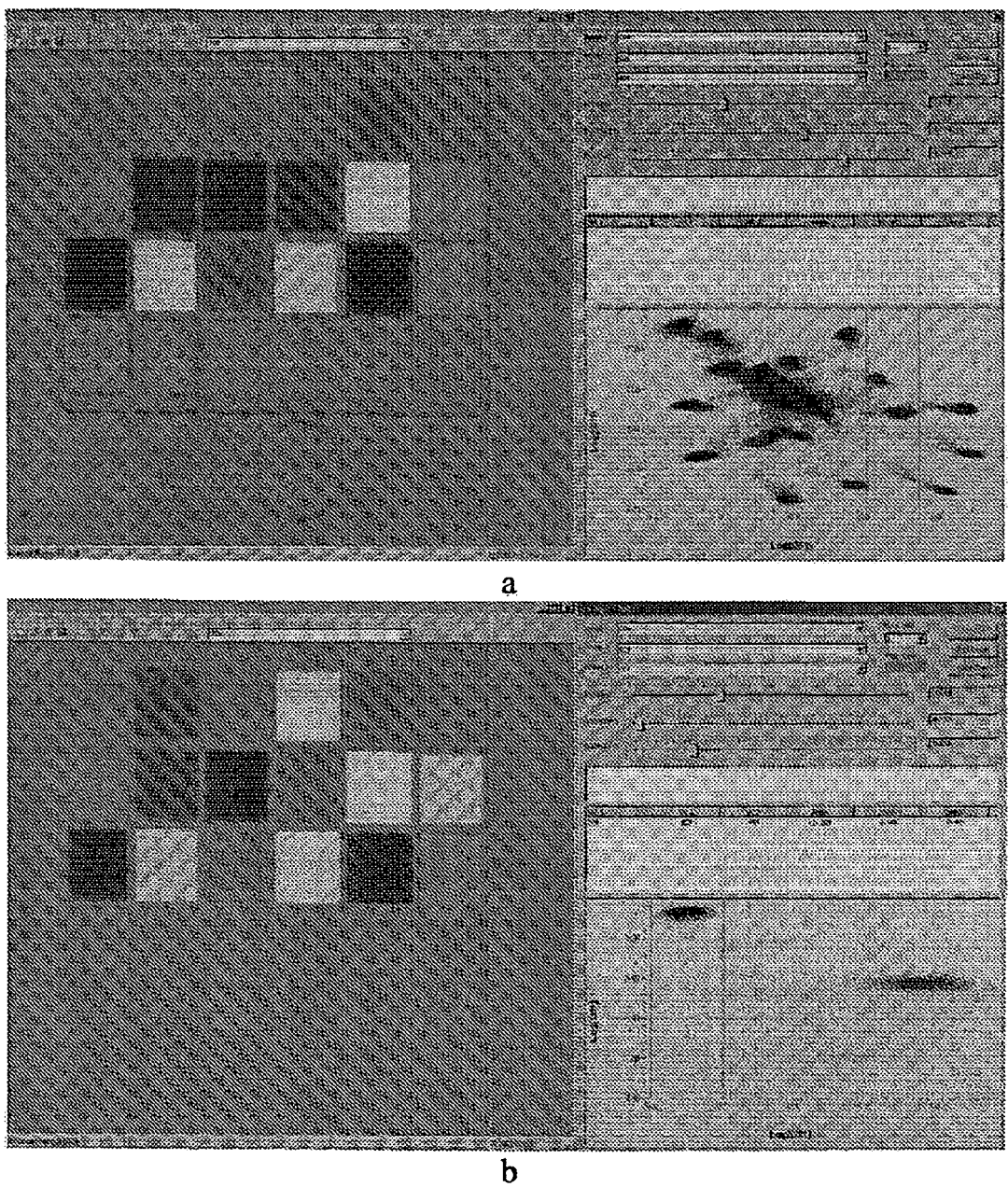
FIG. 7 illustrates a user interface of the present invention displaying the detection of color objects in the delta-logarithmic feature space.

An example of the detection procedure of color objects in the delta-log feature space with the method of the present invention, displayed in user-interface form is shown in FIGS. 7a and 7b. A Macbeth color checker chart is sensed, no calibration, T=3100 K. FIG. 7a corresponds to one wavelength triplet, and FIG. 7b to another. In the lower right hand corner of FIGS. 7a and 7b are the chromaticity maps. The color checker chart is shown on the left in both FIGS. 7a and 7b. In FIG. 7a, the big blob in the center of the chromaticity map represents the shades of gray in the bottom row of the Macbeth color checker, while all 18 colors form more or less compact blobs around the center. In this example detection is done in two passes to illustrate how using additional isochromes for detection can improve detectability. In complex scenes, many band combination and isochromes may be needed for adequate detection and discrimination. In the first case, (FIG. 7a), the band combination is {596, 529, 456 nm}, and the two vertical separators (the vertical lines) define a range or target chromaticity that excludes all other colors but two colors (#4-foliage and #6-bluish green) as it can be seen in the left hand side of FIG. 7a, where the red mask displays the detected objects. In the second case (FIG. 7b), another band combination {596, 529, 497 nm} is added to the detection discrimination parameters, and the bluish green color gets separated from the foliage color rectangle and detected with good rejection of all other colors. Once the detection parameters have been determined, they can be saved and subsequently applied to any image hyper-cube for automated detection of the specific target.

The reason for applicability of the same detection parameter for broad range color temperature light sources is that after applying rotation by angle $\Theta$ to the isochromes they become vertical and all points corresponding to a given color get into the region between two vertical separators. Any change in T moves the points vertically, but does not remove them from the region, selected by the separators.

Figure 8:
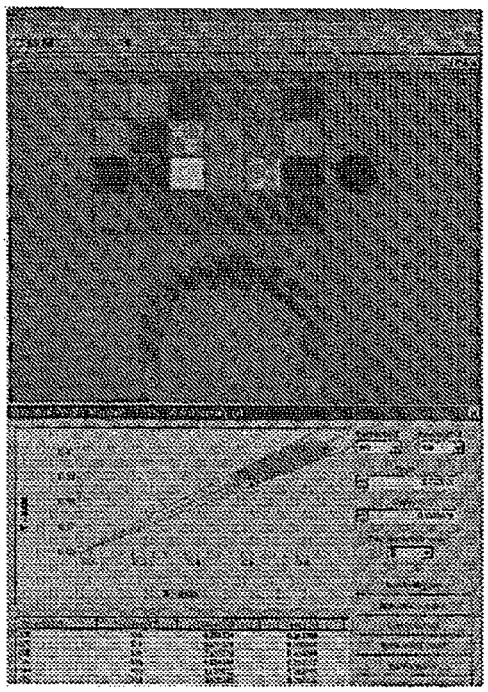
FIGS. 8 a-b demonstrate detection of human skin with traditional detection tool of the prior art (SAM, a: T=3100 K, b: T=1800 K), SAM failed in (b)
Figure 8:
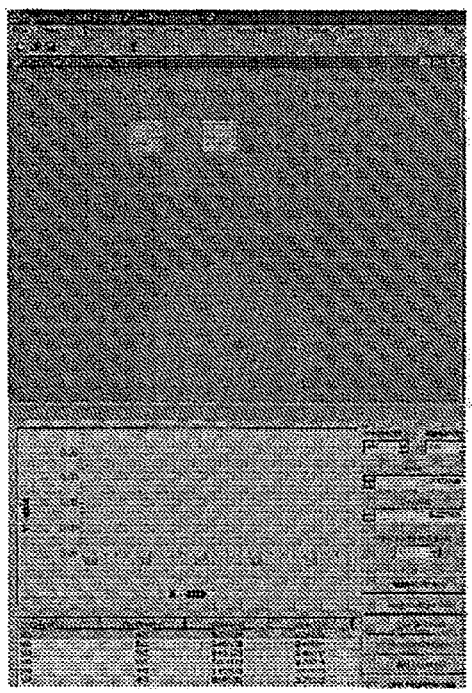
Figure 8:
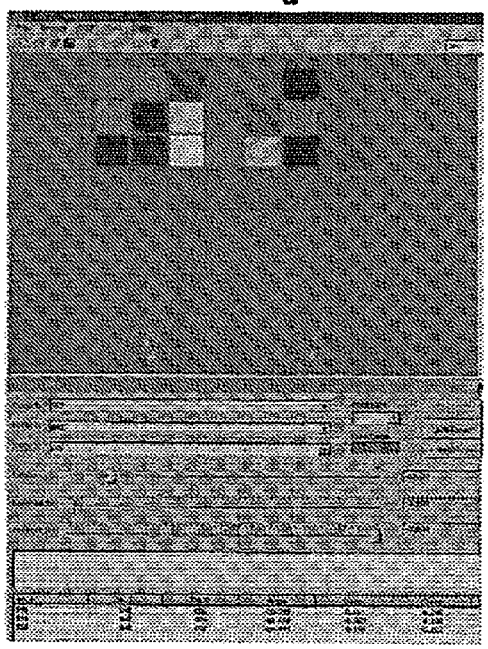
Figure 8:
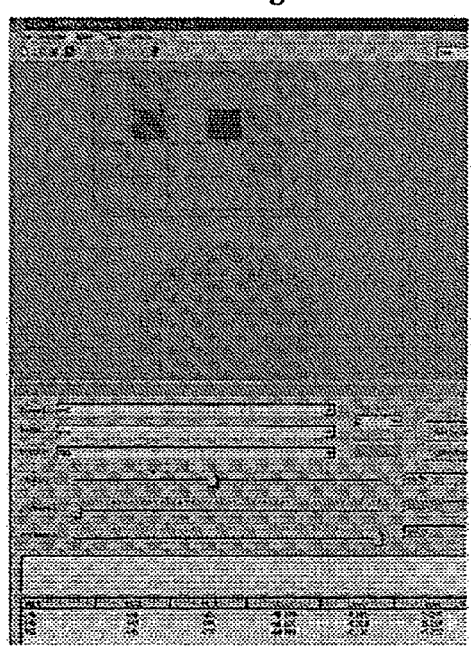

FIGS. 8 a-d illustrate this statement and compares the results of detection with the invented method and with SAM, a well-known standard classifier. Images 8a, and 8c display the same image cube acquired with the 3100 K light source and processed with the SAM and TCE tools respectively. The both tools provide good detection, because the detection parameters were determined for this color temperature. However, when the light source color temperature changes to 1800 K-images 8b and 8d, SAM cannot detect a human target and needs recalibration for new lighting conditions (b), while the method of the present invention still detects the target without any recalibration (d).

One of important parts of the analysis of the situation is assessment of available band combinations and optimization of the set of spectral bands and detection parameters. For the method of the present invention, a proper band selection is crucial, because there are very many combinations of bands and without an adequate selection algorithm it is easy to miss the bands, which are best for detection. As it has been mentioned, the transform into the delta-logarithmic space leads to significant increase of the feature space dimensionality.

Our original image cubes have dimensionality N=32 (the amount of spectral bands in the visible range). The number of coordinate planes $N_f$ in the feature space, on which a pixel spectral vector P can be projected is the number of variation of 32 items taken 2 at a time:

$$N_f = {}_2V_{32} = \frac{32!}{(32-2)!} = 32 \cdot 31 = 992 \quad (10)$$

The band combinations $\{\lambda_i, \lambda_j\}$ and $\{\lambda_j, \lambda_i\}$ are equivalent to each other, so actually there are $N_f/2$ degrees of freedom for selecting bands for detection.

Processing in the delta-logarithmic space brings many more degrees of freedom. The spectral vector can be projected on planes with axes $\ln(P_i/P_k)$, $\ln(P_n/P_m)$, where i, k n, and m are the numbers of spectral bands. They are integers in the range 0<i, k; n, m<N+1. The total amount of degrees of freedom $N_{dl}^q$ can be calculated as the number of variations of 32 items taken 4 at a time:

$$N_{dl}^q = {}_4V_{32} = 32 \cdot 31 \cdot 30 \cdot 29 = 863,040 \quad (11)$$

Not all of these variations, which we call quadruplets, are independent. For example, switching the horizontal and vertical axes in any projection plane does not give any new information, therefore the quadruplet of wavelength $\{\lambda_i, \lambda_n, \lambda_k, \lambda_m\}$, where the first two wavelength are the numerators and the last two are the denominators, and the quadruplet $\{\lambda_n, \lambda_i, \lambda_m, \lambda_k\}$ are identical to each other and one of them can be omitted, but even the half of $N_{dl}^q$ is a large number.

If the denominator is the same for the both coordinate axes $\ln(P_i/P_k)$, $\ln(P_n/P_k)$, a band triplet is used instead of a band quadruplet. A triplet can be written as $\{\lambda_i, \lambda_n, \lambda_k\}$, where the first two wavelength are the numerators and the third is the denominator for the both of them. Instead of (14) we have the following number of possible variations $N_{dl}^t$:

$$N_{dl}^t = {}_3V_{32} = 32 \cdot 31 \cdot 30 = 29760 \quad (12)$$

As with band quadruplets, a half of triplets can be removed, but there are still over 14,000 combinations remain.

Figure 9:
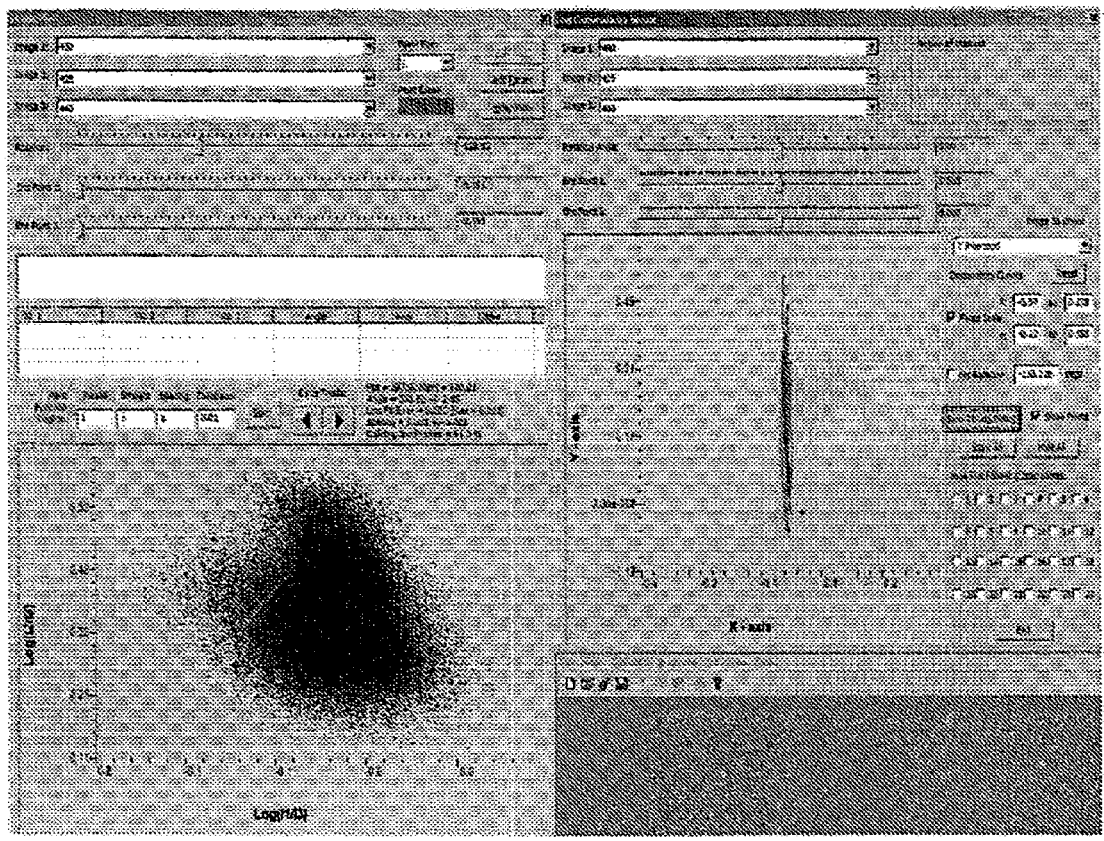
FIG. 9 illustrates a user interface of the present invention displaying an example the feature space for a randomly selected wavelength triplet.

By far not all available band triplets (and quadruplets) are equally useful for detection. For example, FIG. 9 shows a chromaticity map (left hand side) and the isochrome map for a randomly-selected set of wavelength {430, 435, 440 nm} triplet (right hand side) for hyper-cube data for images of the color checker chart in a diverse set of illumination. The figure shows that this triplet is not the best choice for detection as the chromaticity map is a single "blob" (all classes are mixed), and the isochromes are overlapped (not separated). The classes corresponding to them cannot be by this reason separated.

Figure 10:
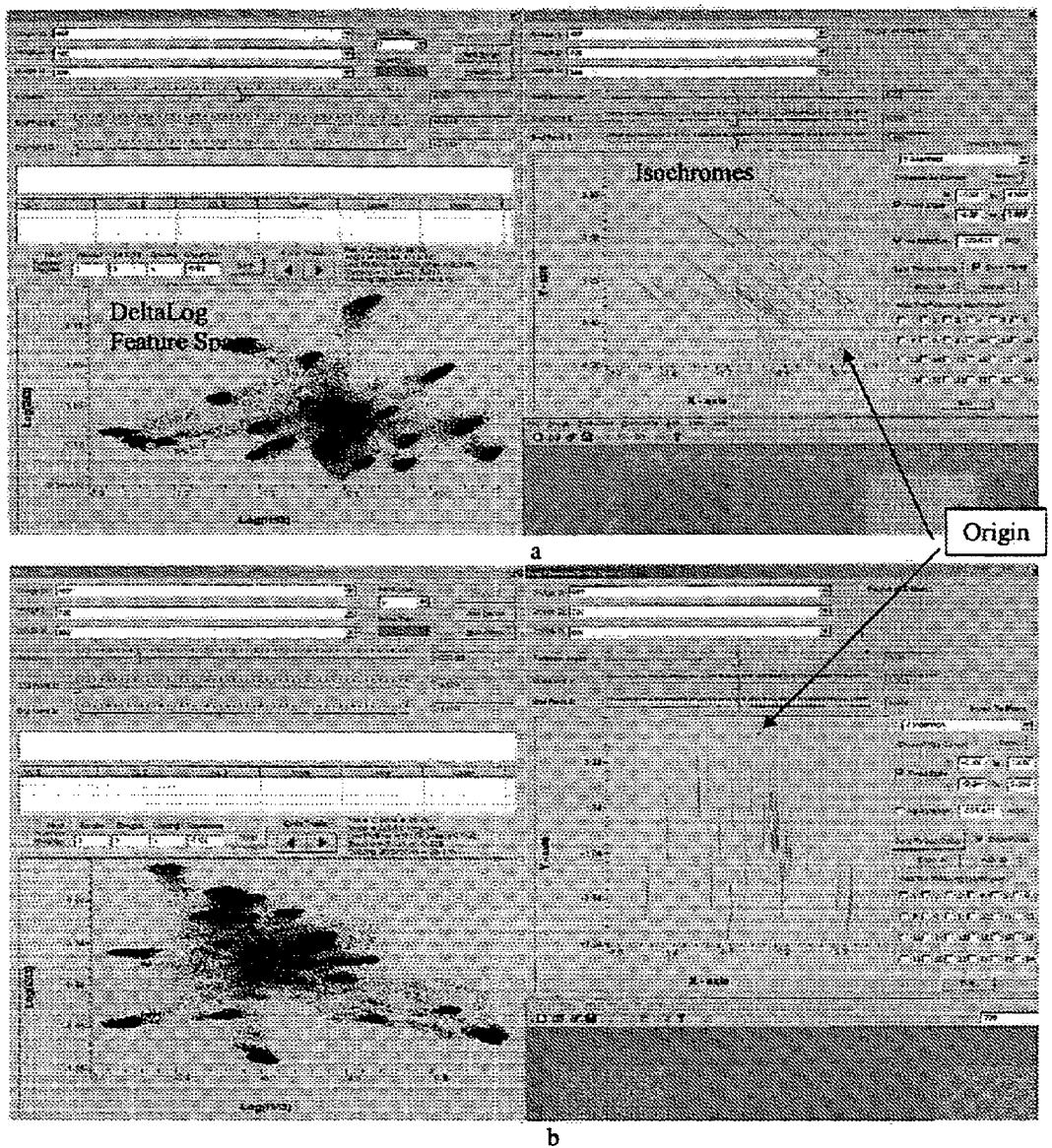
FIGS. 10 a-b illustrates a user interface of the present invention displaying an example of the feature space for a selected and preferred triplet.

An example of a preferred detection triplet is shown in FIGS. 10a and 10b {427, 720, 596 nm} with chromaticity maps on the left hand side, and isochrome maps on the right hand side. Also, in this case the color checker chart is sensed in diverse illumination. The raw data for the isochromes show that they are tilted, straight, parallel to each other, and well separated, so after the rotation transform they all become vertical and the targets can be easily detected based on target chromaticity for any light source color temperature in the range of 1200-3100 K. The target chromacity changes along the horizontal axis, while the lighting chromacity changes along the vertical axis.

Figure 11:
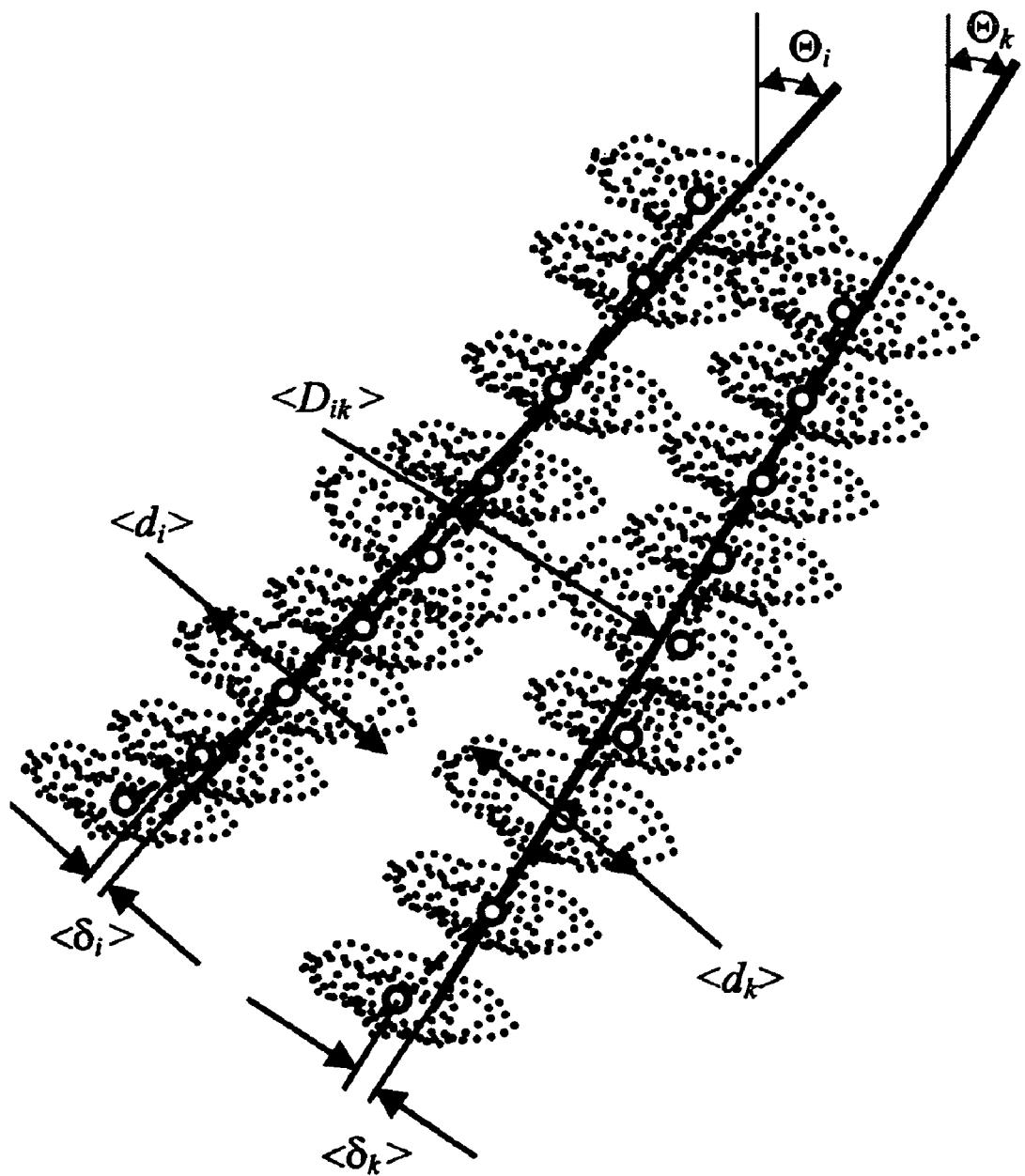
FIG. 11 illustrates the three criteria for sorting and ranking the wavelength band combinations according to the present invention.

In a preferred embodiment, the use of a Tri-Criteria sorting is found to provide a ranking for reliable selection of band combinations and isochromes for high probability detection. Detailed analysis has shown that there are several criteria for sorting and optimization of spectral triplets for successful target detection. Among these, the most preferred are that the isochromes must be readily fit to straight lines with small mean error deviations, parallel to each other, and separated by sufficient distance so that the mean square deviation from the fit line is less than half of the separation distance. Based on this, we can write mathematical expressions for the criteria. They are also depicted for a pair of isochromes i and k in FIG. 11:

Criterion 1. The minimum value of the mean error $\langle\epsilon\rangle_{\{i,k,m\}}$ of linear fitting the isochromes:

$$\min[\langle\delta\rangle_{\{i,k,m\}}], \quad (13)$$

Criterion 2. The isochromes being most parallel to each other corresponds to the minimum difference in the angles of tilt (slope) $\Theta$:

$$\min\left(\Delta_{ik} = \sum_{k=1}^{k=N}\sum_{i=1}^{i=N}(\Theta_i - \Theta_k)\right) \quad (14)$$

Criterion 3. The distance between adjacent isochromes $\langle D_{ik}\rangle$ must be greater than the one-half of the sum of the mean dispersion of the corresponding classes $(\langle d_i \rangle + \langle d_k \rangle)/2$ to avoid overlapping of the blobs of each isochrome:

$$\min[O_{ik} = (\langle d_i \rangle + \langle d_k \rangle)/(2 \langle D_{ik} \rangle)] \quad (15)$$

Conditions (13), (14), and (15) can be combined in a merit function M, which must be minimized for triplet selection:

$$M = \alpha \langle \delta \rangle_{\{i,k,m\}} + \beta \Delta_{ik} + \gamma O_{ik}, \quad (16)$$

where $\alpha$, $\beta$, and $\gamma$ are the weights for the included parameters. The weights can be optimized for the best sorting, isochrome and band combination selection, and detection by testing over the data set which is used to determine known target, material, or object chromaticity. In a preferred embodiment, the weights are equal. For the merit function of Eqn. 16, the highest ranked and most advantageous band combination would have the least value of M.

Figure 12:
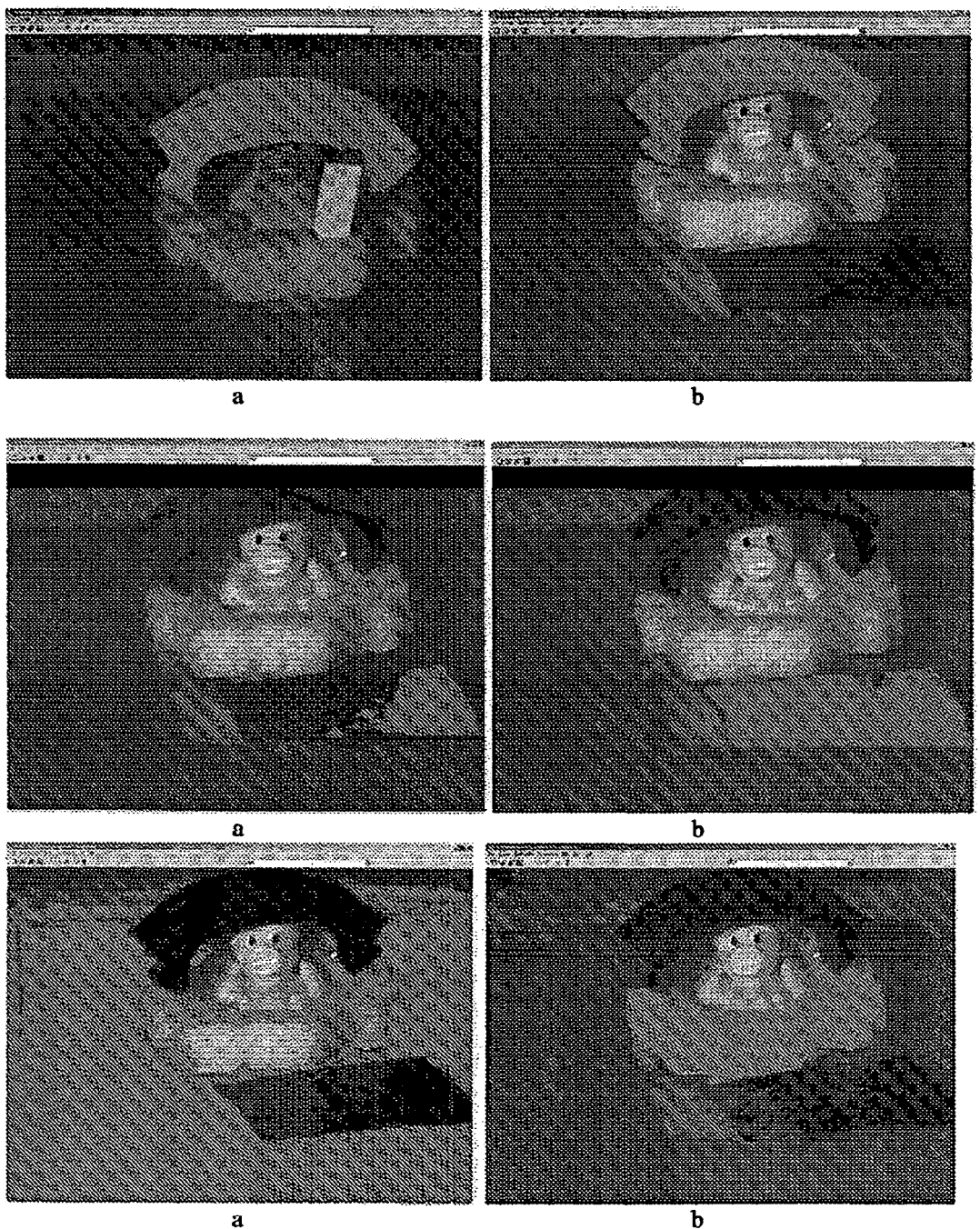
FIG. 12 illustrates detection of dark objects in the delta-logarithmic feature space according to the present invention; the pixels classified as "target" are shown in color.
Figure 13:
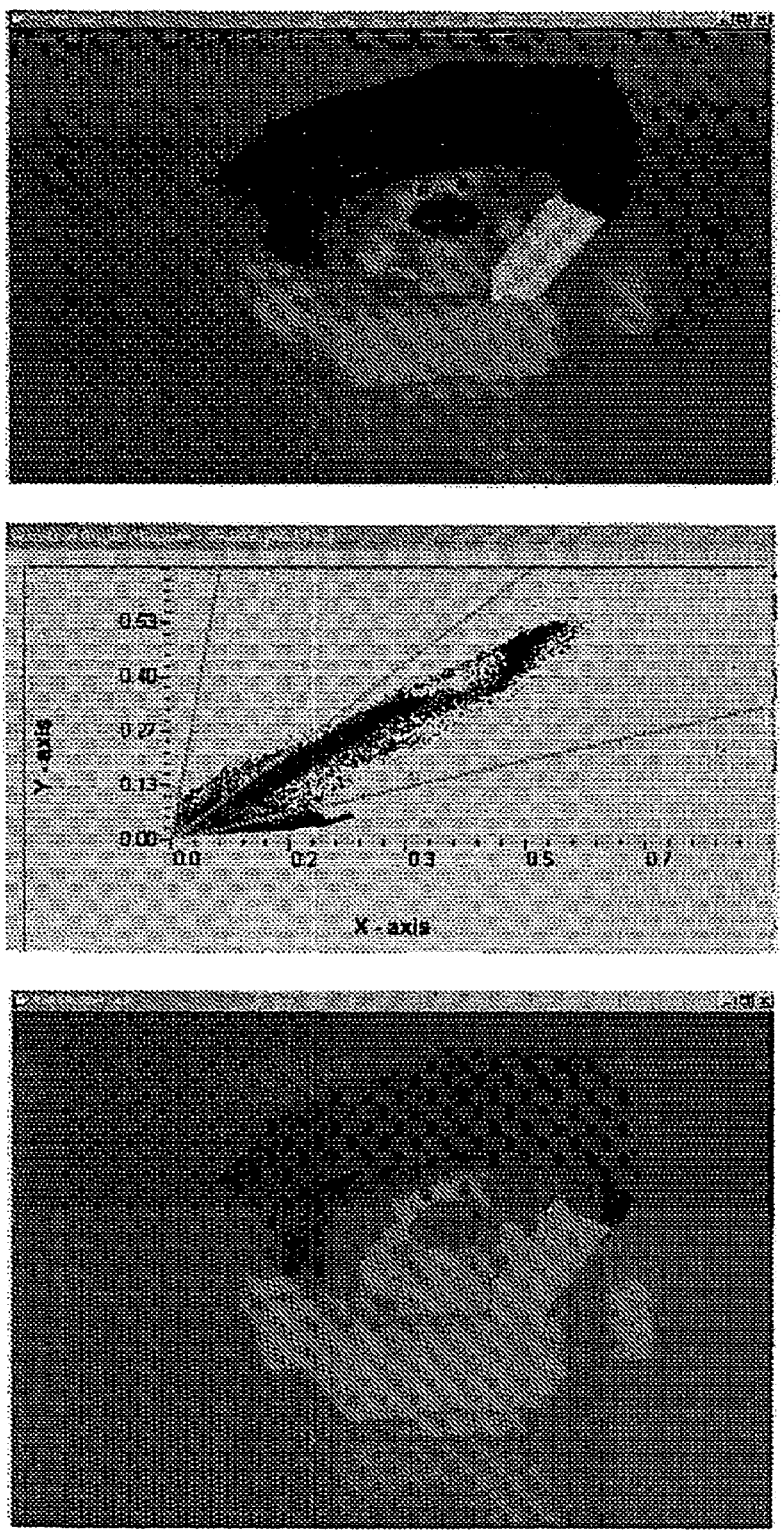
FIG. 13 illustrates the unreliable detection of dark objects using SAM according to the prior art.

The method of this specification has been shown to work well for the detection of 'dark' objects, i.e., objects viewed in scenes with poor illumination. FIGS. 12a and 12b show the method can detect a variety of dark objects in a scene, e.g., tarp, floater (toy duck), foam sponge, water, etc, according to the discriminants (detection parameters) that are used. In FIG. 12a, detection parameters are set for (top picture) tarp, (middle picture) tarp on surface of the water, and (bottom picture) water. In FIG. 12b, detection parameters are set for (top picture) tarp, (middle picture) partially submerged and surface tarp, and (bottom picture) foam sponge. (There is a calibration panel in the pictures in FIG. 12a that is located to the right of the "floater". This calibration panel was not used in the detection method described herein.) A reason for this success is that the logarithmic transform extends the useful dynamic range for detection. In contrast, conventional methods, such as SAM, which is applied in linear feature space, have limited success in the detection of dark objects. The failure of SAM is seen in FIG. 13 (middle), wherein a plot of linear feature space shows that the dark objects to be situated very close to the origin and are crowded together. As a consequence, dark objects are difficult to detect and it is difficult to accurately detect them as separate objects, and also to discriminate between a particular object and the background.

FIG. 13 (top) shows a monochrome (a wavelength single band) picture of the scene, which includes a tarp covered "floater", a foam sponge, a calibration panel, and water. The failure of the prior art SAM to discriminate is seen in the bottom picture of FIG. 13 where there is poor discrimination of foam sponge from features on the floater (duck) and reflection on the water surface.

The method has been applied to the successful detection of humans by hyperspectral imaging and detection of human skin and other bio-metric characteristics and features. The method has been used in the spectral range from 420 nm to 720 nm. For illumination by common light sources and in common ambient conditions and within the validity of parameter constraints, e.g., on TX used for approximation of the Planck distribution, it is expected to be practical and useful in the spectral range from the deep ultraviolet through the short wave infrared. It is further anticipated that the results, demonstrations, and techniques described herein are to be considered representative and may be replaced by equivalent and other methods that are well known in the art.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method for hyper-spectral or multi-spectral data classification or target detection in diverse lighting conditions with an invariant set of detection parameters, based on decoupling target chromaticity and lighting chromaticity in a delta-logarithmic feature space and comprising the steps of:

acquiring two or more multi-spectral or hyperspectral image data, each set being an image hyper-cube for a scene and the two sets having been acquired with illumination having different chromaticity;

performing a logarithmic transform of the acquired image hyper-cubes;

calculating chromaticity maps for all triplets or quadruplets of wavelengths, each said triplet or quadruplet comprising a "band combination", and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space, then determining isochrome lines for each band combination;

sorting all band combinations by merit function values, the value of each band combination being calculated as a function of the value of at least one criteria that are applied to the isochromes, and the sorting being the ranking of the band combinations according to their merit function value, the greatest rank being given to the most advantageous merit function value;

comparing presumed-target chromaticities in a subset of feature space that corresponds to one or more of the highest ranked band combinations with classification or detection discriminant parameters; and generating a detection mask through the denotation of the subset of pixels that have been identified or classified, as having a chromaticity that sufficiently matches the detection discriminant parameters.

2. The method of claim 1 in which the sorting by merit function values is according to Tri-Criteria or Multi-Criteria evaluation.

3. The method of claim 2 in which the Tri-Criteria or Multi-Criteria are selected from a group consisting of one or more of the following: a function of the minimum value of the mean error of linear fitting the isochromes, a function of the minimum difference in the angles of tilt (slopes) of the isochromes, a function of the ratio of the distance between adjacent isochromes and the sum of the mean dispersion of the corresponding classes.

4. The method of claim 1 in which the resulting isochromes are rotated to a vertical orientation.

5. The method of claim 1 with the additional step of:

registering or outputting the results of detection, for example exhibiting the results as a display, or storing the results in a memory, or generating a signal such as an alarm.

6. A method for hyper-spectral or multi-spectral data classification and target signature determination, based on decoupling target chromaticity and lighting chromaticity in a delta-logarithmic feature space and comprising the steps of:

acquiring a plurality of sets of image hyper-cube data of at least one scene, each of said scenes containing the target or material of interest, the data sets differing by their illumination, which has different light chromaticity for the different data sets;

performing a logarithmic transform of the said acquired image hyper-cubes, resulting in hyper-cubes with each element being the logarithm of the corresponding pixel value;

calculating chromaticity maps for all triplets or quadruplets of wavelengths, each said triplet or quadruplet comprising a "band combination", and each element of the map corresponding to a pixel, or group of pixels, i.e., a region of interest, treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space, then determining isochrome lines for each band combination;

sorting all band combinations by merit function values, the value of each band combination being calculated as a function of the value of at least one criteria that are applied to the isochromes, and the sorting being the ordering of the band combinations according to their merit function value, the greatest rank being given to the most advantageous merit function value; and selecting a set containing one or more of the highest ranked band combinations, this set corresponding to a set of projection planes of a subspace of feature space, and identifying one or more isochromes in the subspace of feature space, and the identified isochromes and band combinations comprising the target signature.

7. The method of claim 6 wherein the target data comprise hyper-spectral images of a color chart.

8. The method of claim 6 in which the resulting isochromes are rotated to a vertical orientation.

9. The method of claim 6 in which the sorting criteria are selected from a group comprising one or more of the following: a function of the minimum value of the mean error of linear fitting the isochromes, a function of the minimum difference in the angles of tilt (slopes) of the isochromes, a function of the ratio of the distance between adjacent isochromes and the sum of the mean dispersion of the corresponding classes.

10. A method for hyper-spectral or multi-spectral data classification or target detection in diverse lighting conditions with an invariant set of classification parameters, based on decoupling target chromaticity and lighting chromaticity in a delta-logarithmic feature space and comprising the steps of:

acquisition of image hyper-cube data and data correction as described above for a known target, material, object, or color calibration chart in various lighting conditions that correspond to various color temperatures;

performing a logarithmic transform of the acquired image hyper-cube data, the result is a hyper-cube with each element being the logarithm of the corresponding pixel value;

calculating chromaticity maps for all triplets or quadruplets of wavelengths, each said triplet or quadruplet comprising a "band combination", and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space according to the equation ln $$P_{kl} = \ln\left[\frac{P_k}{P_l}\right] = \ln P_k - \ln P_l = R_k - R_l - \frac{L_k - L_l}{T},$$

and, the resulting isochromes being rotated to a vertical orientation where selected;

sorting all band combinations by merit function values, the value of each band combination being calculated as a function of the value set of at least one criteria that are applied to the isochromes, and the sorting being the ordering of the band combinations according to their merit function value, the greatest rank being given to the most advantageous merit function value;

selection of a subset comprising one or more of the highest ranked band combinations, which define a feature subspace, and storage of these bands in a feature subspace band combination list and also storage of classification or detection discriminant parameters comprising the target isochromes and their spacing from neighboring non-target isochromes in the feature subspace of these band combinations;

acquisition of image hyper-cube data and data correction for a scene that is to be searched for targets, specific materials, or specific objects, this scene being referred to as a "search scene";

performing a logarithmic transform of the acquired image hyper-cube data of the search scene;

calculating chromaticity maps for the feature subspace, i.e., for the subset of band combinations selected above, and each element of the map corresponding to a pixel, or group of pixels treated as a single element, with the map coordinates each being the logarithm of the ratio of the pixel values at two of the different wavelengths of the triplet or quadruplet, the logarithm of the ratio of the pixel values being the spectral band subtraction in the logarithmic feature space, and where a rotational transform was applied to the isochrome map, then, applying the same rotational transform for that band combination;

comparing presumed-target chromaticities in the feature subspace with the above identified classification or detection discriminant parameters that represent a known target, material or object.

11. The method of claim 10 with the additional step of:

generating a detection mask through the denotation of the subset of pixels that have been identified as having a chromaticity that sufficiently matches the classification or detection discriminant parameters.

12. The method of claim 1 wherein the lighting chromaticity is measured as a function of equivalent color temperature that is based on a Planckian or near-Planckian distribution.

13. The method of claim 1 wherein the spectral range of measurement is in the short wavelength approximation, which is defined as $$\exp\left(\frac{c_2}{T\lambda}\right) \gg 1,$$

and where $c_2 = 1.44 \cdot 10^{-2}$ K·m, wherein T is the temperature of the black body radiator in K, and $\lambda$ is the wavelength in m.

14. The method of claim 1 wherein the spectral range of measurement is in the long wavelength approximation, which is defined as $T\lambda \ll 1$.

15. The use of the method of claim 1 for determining the reflectance of an object in a scene by analysis of hyperspectral or multi-spectral image data for a plurality of conditions of illumination with different color temperatures.

16. The use of the method of claim 1 for determining the thermal emissivity of an object in a scene.

* * * * *